(12) United States Patent
Alves et al.

(10) Patent No.: US 12,138,298 B2
(45) Date of Patent: Nov. 12, 2024

(54) EXPRESSION VECTOR FOR CHOLESTEROL 24-HYDROLASE IN THERAPY OF POLYGLUTAMINE REPEAT SPINOCEREBELLAR ATAXIAS

(71) Applicants: BRAINVECTIS, Paris (FR); INSERM (INSTITUT NATIONAL DE LA SANTÉ ET DE LA RECHERCHE MÉDICALE), Paris (FR); UNIVERSIDADE DE COIMBRA, Coimbra (PT); CENTRO DE NEUROCIÊNCIAS E BIOLOGIA CELULAR, Coimbra (PT)

(72) Inventors: Sandro Alves, Paris (FR); Nathalie Cartier-Lacave, Paris (FR); Luis Pereira De Almeida, Coimbra (PT); Clévio Nobrega, Coimbra (PT); Liliana Mendonça, Coimbra (PT)

(73) Assignees: BRAINVECTIS, Paris (FR); INSERM (INSTITUT NATIONAL DE LA SANTÉET DE LA RECHERCHE MÉDICALE), Paris (FR); UNIVERSIDADE DE COIMBRA, Coimbra (PT); CENTRO DE NEUROCIÊNCIAS BIOLOGIA CELULAR, Coimbra (PT)

( * ) Notice: Subject to any disclaimer, the term of this patent is extended or adjusted under 35 U.S.C. 154(b) by 250 days.

(21) Appl. No.: 16/480,541

(22) PCT Filed: Jan. 30, 2018

(86) PCT No.: PCT/EP2018/052199
§ 371 (c)(1),
(2) Date: Jul. 24, 2019

(87) PCT Pub. No.: WO2018/138371
PCT Pub. Date: Aug. 2, 2018

(65) Prior Publication Data
US 2019/0343927 A1 Nov. 14, 2019

(30) Foreign Application Priority Data

Jan. 30, 2017 (EP) .................................. 17305100

(51) Int. Cl.
*A61K 38/44* (2006.01)
*A61K 48/00* (2006.01)
*A61P 25/28* (2006.01)
*C12N 7/00* (2006.01)
*C12N 15/86* (2006.01)

(52) U.S. Cl.
CPC .......... *A61K 38/44* (2013.01); *A61K 48/0075* (2013.01); *A61P 25/28* (2018.01); *C12N 7/00* (2013.01); *C12N 15/86* (2013.01); *C12Y 114/13098* (2013.01); *A61K 48/00* (2013.01); *C12N 2750/14143* (2013.01); *C12N 2750/14171* (2013.01)

(58) Field of Classification Search
CPC .... A61K 38/44; A61K 48/0075; A61K 48/00; A61K 9/0085; A61K 31/713; A61P 25/28; C12N 7/00; C12N 15/86; C12N 2750/14143; C12N 2750/14171; C12N 9/0073; C12Y 114/13098; A01K 2267/0318
See application file for complete search history.

(56) References Cited

U.S. PATENT DOCUMENTS

| | | |
|---|---|---|
| 4,861,719 A | 8/1989 | Miller |
| 5,139,941 A | 8/1992 | Muzyczka et al. |
| 5,173,414 A | 12/1992 | Lebkowski et al. |
| 5,278,056 A | 1/1994 | Bank et al. |
| 5,882,877 A | 3/1999 | Gregory et al. |
| 6,013,516 A | 1/2000 | Verma et al. |
| 6,127,175 A | 10/2000 | Mgne et al. |
| 6,464,998 B1 | 10/2002 | Beuzard et al. |
| 8,198,257 B2 | 6/2012 | Aubourg et al. |
| 9,132,173 B2 | 9/2015 | Caboche et al. |
| 2013/0209410 A1* | 8/2013 | Caboche ................. A61P 43/00 424/93.2 |
| 2017/0044590 A1 | 2/2017 | Haldar et al. |
| 2019/0343927 A1 | 11/2019 | Alves et al. |
| 2022/0054597 A1 | 2/2022 | Piguet et al. |

FOREIGN PATENT DOCUMENTS

| | | |
|---|---|---|
| CN | 105682688 A | 6/2016 |
| EP | 3388520 A1 | 10/2018 |
| JP | 2013-544236 A | 4/2012 |

(Continued)

OTHER PUBLICATIONS

Ayciriex et al. "Neuronal cholesterol accumulation induced by Cyp46a1 down-regulation in mouse hippocampus disrupts brain lipid homeostasis." Frontiers in molecular neuroscience (10)1-15 (2017).

(Continued)

*Primary Examiner* — Jeremy C Flinders
*Assistant Examiner* — Alexander W Nicol
(74) *Attorney, Agent, or Firm* — NIXON PEABODY LLP; Ronald I. Eisenstein; Shayne Y. Huff

(57) ABSTRACT

The present invention relates to a vector for use in the treatment of a polyglutamine repeat spinocerebellar ataxia, which vector comprises cholesterol 24-hydroxylase encoding nucleic acid.

Figure 1:

14 Claims, 5 Drawing Sheets
(5 of 5 Drawing Sheet(s) Filed in Color)
Specification includes a Sequence Listing.

(56) References Cited

FOREIGN PATENT DOCUMENTS

| WO | 1992001070 A1 | 1/1992 |
|---|---|---|
| WO | 19930003769 A1 | 3/1993 |
| WO | 1994019478 A1 | 9/1994 |
| WO | 1995014785 A1 | 6/1995 |
| WO | 1996022378 A1 | 7/1996 |
| WO | 2009/034127 A1 | 3/2009 |
| WO | 2012/049314 A1 | 4/2012 |
| WO | 2014210389 A1 | 12/2014 |
| WO | 2016049110 A1 | 3/2016 |
| WO | 2017100671 A1 | 6/2017 |
| WO | 2018138371 A1 | 8/2018 |
| WO | 2018226785 A1 | 12/2018 |
| WO | 2020089154 A1 | 5/2020 |

OTHER PUBLICATIONS

Djelti et al. "CYP46A1 inhibition, brain cholesterol accumulation and neurodegeneration pave the way for Alzheimer's disease." Brain 138(8): 2383-2398 (2015).

Russell et al. "Cholesterol 24-hydroxylase: an enzyme of cholesterol turnover in the brain." Annual review of biochemistry (78): 1017-1040 (2009).

Alves et al. "Allele-specific RNA silencing of mutant ataxin-3 mediates neuroprotection in a rat model of Machado-Joseph disease." PloS one 3(10): e3341 pp. 1-10 (2008).

Alves et al. "Silencing ataxin-3 mitigates degeneration in a rat model of Machado-Joseph disease: no role for wild-type ataxin-3 ?." Human Molecular Genetics 19(12): 2380-2394 (2008).

Alves et al. "Striatal and nigral pathology in a lentiviral rat model of Machado-Joseph disease." Human Molecular Genetics 17(14): 2071-2083 (2010).

Belur et al. "Intranasal adeno-associated virus mediated gene delivery and expression of human iduronidase in the central nervous system: a noninvasive and effective approach for prevention of neurologic disease in mucopolysaccharidosis type I." Human gene therapy 28(7): 576-587 (2017).

Björkhem et al. "Cholesterol homeostasis in human brain: turnover of 24S-hydroxycholesterol and evidence for a cerebral origin of most of this oxysterol in the circulation." Journal of Lipid Research 39(8): 1594-1600 (1998).

Bürk et al. "Autosomal dominant cerebellar ataxia type I: oculomotor abnormalities in families with SCA1, SCA2, and SCA3." Journal of Neurology 246(9): 789-797 (1999).

Chan et al. "Engineered AAVs for efficient noninvasive gene delivery to the central and peripheral nervous systems." Nature neuroscience 20(8): 1172-1179 (2017).

Chevy et al. "Sterol profiling of amniotic fluid: a routine method for the detection of distal cholesterol synthesis deficit." Prenatal Diagnosis: Published in Affiliation With the International Society for Prenatal Diagnosis 25(11): 1000-1006 (2005).

Deverman et al. "Cre-dependent selection yields AAV variants for widespread gene transfer to the adult brain." Nature Biotechnology 34(2): 204-209 (2016).

Durr et al. "Spinocerebellar ataxia 3 and Machado-Joseph disease: clinical, molecular, and neuropathological features." Annals of Neurology 39(4): 490-499 (1996).

Dzeletovic et al. "Time course of oxysterol formation during in vitro oxidation of low density lipoprotein." Chemistry and Physics of Lipids 78(2): 119-128 (1995).

Elverman et al. "Prolonged benefit from systemic rAAV8 in a canine model of myotubular myopathy." Neuromuscular Disorders (26): S198-199 (2016).

Foust et al. "Intravascular AAV9 preferentially targets neonatal neurons and adult astrocytes." Nature biotechnology 27(1): 59-65 (2009).

GenBank. "*Homo sapiens* cholesterol 24-hydroxylase mRNA, complete cds." Database accession No. AF094480. (1999).

Hudry et al. "Adeno-associated virus gene therapy with cholesterol 24-hydroxylase reduces the amyloid pathology before or after the onset of amyloid plaques in mouse models of Alzheimer's disease." Molecular Therapy 18(1): 44-53 (2010).

Kawaguchi et al. "CAG expansions in a novel gene for Machado-Joseph disease at chromosome 14q32. 1." Nature Genetics 8(3): 221-228 (1994).

Klockgether et al. "Autosomal dominant cerebellar ataxia type I. MRI-based volumetry of posterior fossa structures and basal ganglia in spinocerebellar ataxia types 1, 2 and 3." Brain: a Journal of Neurology 121(9): 1687-1693 (1998).

Kyrkanides et al. "β-hexosaminidase lentiviral vectors: transfer into the CNS via systemic administration." Molecular brain research 133(2): 286-298 (2005).

Mccarty et al. "Self-complementary recombinant adeno-associated virus (scAAV) vectors promote efficient transduction independently of DNA synthesis." Gene Therapy 8(16): 1248-1254 (2001).

Mendell et al. "480. Gene therapy for spinal muscular atrophy type 1 shows potential to improve survival and motor functional outcomes." Molecular Therapy (24): S190 (2016).

Nóbrega et al. "Overexpression of mutant ataxin-3 in mouse cerebellum induces ataxia and cerebellar neuropathology." The Cerebellum 12(4): 441-455 (2013).

Orr et al. "Trinucleotide repeat disorders." Annu Rev Neurosci. 30: 575-621 (2007).

Oue et al. "Characterization of mutant mice that express polyglutamine in cerebellar Purkinje cells." Brain Research 1255: 9-17 (2009).

Rub et al. "Clinical features, neurogenetics and neuropathology of the polyglutamine spinocerebellar ataxias type 1, 2, 3, 6 and 7." Progress in neurobiology (104): 38-66 (2013).

Rúb et al. "Degeneration of ingestion-related brainstem nuclei in spinocerebellar ataxia type 2, 3, 6 and 7." Neuropathology and Applied Neurobiology 32(6): 635-649 (2006).

Rúb et al. "New insights into the pathoanatomy of spinocerebellar ataxia type 3 (Machado-Joseph disease)." Current Opinion in Neurology 21(2): 111-116 (2008).

Schöls et al. "Autosomal dominant cerebellar ataxia: phenotypic differences in genetically defined subtypes?." Annals of Neurology: Official Journal of the American Neurological Association and the Child Neurology Society 42(6): 924-932 (1997).

Schöls et al. "Autosomal dominant cerebellar ataxias: clinical features, genetics, and pathogenesis." The Lancet Neurology 3(5): 291-304 (2004).

Torashima et al. "Lentivector-mediated rescue from cerebellar ataxia in a mouse model of spinocerebellar ataxia." EMBO Reports 9(4): 393-399 (2008).

Yue et al. "Safe and bodywide muscle transduction in young adult Duchenne muscular dystrophy dogs with adeno-associated virus." Human molecular genetics 24(20): 5880-5890 (2015).

Zhang et al. "Several rAAV vectors efficiently cross the blood-brain barrier and transduce neurons and astrocytes in the neonatal mouse central nervous system." Molecular Therapy 19(8): 1440-1448 (2011).

Alves et al. "The autophagy/lysosome pathway is impaired in SCA7 patients and SCA7 knock-in mice." Acta neuropathologica 128(5): 705-722 (2014).

Boussicault et al. "CYP46A1, the rate-limiting enzyme for cholesterol degradation, is neuroprotective in Huntington's disease." Brain 139(3): 953-970 (2016).

Menzies et al. "Autophagy induction reduces mutant ataxin-3 levels and toxicity in a mouse model of spinocerebellar ataxia type 3." Brain 133(1): 93-104 (2010).

Moutinho et al. "Cholesterol 24-hydroxylase: Brain cholesterol metabolism and beyond." Biochimica et Biophysica Acta (BBA)—Molecular and Cell Biology of Lipids 1861(12): 1911-1920 (2016).

Hueng-Chuen Fan et al: "Polyglutamine (PolyQ) Diseases: Genetics to Treatments", Cell Transplantation, vol. 23, No. 4, Apr. 9, 2014 (Apr. 9, 2014), pp. 441-458.

Lukas C et al: "Spinal cord atrophy in spinocerebellar ataxia type 3 and 6; Impact on clinical disability", Journal of Neurology, Steinkopff-Verlag, DA, vol. 255, No. 8, Jun. 5, 2008 (Jun. 5, 2008), pp. 1244-1249.

(56) References Cited

OTHER PUBLICATIONS

Dayton et al., "More expansive gene transfer to the rat CNS: AAV PHP. EB vector dose—response and comparison to AAV PHP. B." Gene therapy 25.5: 392-400 (2018).

Gadalla et al., "Development of a novel AAV gene therapy cassette with improved safety features and efficacy in a mouse model of Rett syndrome." Molecular Therapy—Methods & Clinical Development 5: 180-190 (2017).

Gadalla et al., "Gene therapy for Rett syndrome: prospects and challenges", Future Neurology, vol. 10, No. 5, p. 467-484, (2015).

Gadalla et al., "Improved survival and reduced phenotypic severity following AAV9/MECP2 gene transfer to neonatal and juvenile male Mecp2 knockout mice." Molecular Therapy 21.1: 18-30 (2013).

Garg et al., "Systemic delivery of MeCP2 rescues behavioral and cellular deficits in female mouse models of Rett syndrome." Journal of Neuroscience 33.34: 13612-13620 (2013).

Guy et al., "A Mouse Mecp2-Null Mutation Causes Neurological Symptoms That Mimic Rett Syndrome." Nature Genetics 27(3): 322-26 (2001).

Katsuno et al. "Getting a handle on Huntington's disease: the case for cholesterol." Nature Medicine 15(3): 253-254 (2009).

Lopez et al., "Suppression of brain cholesterol synthesis in male Mecp2-deficient mice is age dependent and not accompanied by a concurrent change in the rate of fatty acid synthesis." Brain research 1654: 77-84 (2017).

Lutjohann et al., "Identification of Correlative Shifts in Indices of Brain Cholesterol Metabolism in the C57BL6/Mecp2tm1.1Bird Mouse, a Model for Rett Syndrome." Lipids 53.4: 363-373 (2018).

Na et al., "The impact of MeCP2 loss- or gain-of-function on synaptic plasticity." Neuropsychopharmacology 38.1: 212-219 (2013).

Nagy et al., "Cholesterol metabolism and Rett syndrome pathogenesis." Nature Genetics 45.9: 965-967 (2013).

Sellier et al., "Loss of C9 ORF 72 impairs autophagy and synergizes with polyQ Ataxin-2 to induce motor neuron dysfunction and cell death." The EMBO journal 35.12: 1276-1297 (2016).

Tanguy et al., "Systemic AAVrh10 provides higher transgene expression than AAV9 in the brain and the spinal cord of neonatal mice." Frontiers in molecular neuroscience 8 (2015).

Vashi et al., "Treating Rett syndrome: from mouse models to human therapies." Mammalian Genome 30: 90-110 (2019).

Villani et al. "Lovastatin fails to improve motor performance and survival in methyl-CpG-binding protein2-null mice." elife 5: e22409 (2016).

Lund et al., "Knockout of the cholesterol 24-hydroxylase gene in mice reveals a brain-specific mechanism of cholesterol turnover." Journal of Biological Chemistry 278.25: 22980-22988 (2003).

Shafaati et al., "Enhanced production of 24S-hydroxycholesterol is not sufficient to drive liver X receptor target genes in vivo." Journal of internal medicine 270.4: 377-387 (2011).

\* cited by examiner

SEQUENCE LISTING

<160> NUMBER OF SEQ ID NOS: 2

<210> SEQ ID NO 1
<211> LENGTH: 1503
<212> TYPE: DNA
<213> ORGANISM: Homo sapiens
<220> FEATURE:
<221> NAME/KEY: CDS
<222> LOCATION: (1)..(1503)

<400> SEQUENCE: 1

| | | | | | | | | | | | | | | | | |
|---|---|---|---|---|---|---|---|---|---|---|---|---|---|---|---|---|
| atg | agc | ccc | ggg | ctg | ctg | ctg | ctc | ggc | agc | gcc | gtc | ctg | ctc | gcc | ttc | 48 |
| Met | Ser | Pro | Gly | Leu | Leu | Leu | Leu | Gly | Ser | Ala | Val | Leu | Leu | Ala | Phe | |
| 1 | | | | 5 | | | | | 10 | | | | | 15 | | |
| ggc | ctc | tgc | tgc | acc | ttc | gtg | cac | cgc | gct | cgc | agc | cgc | tac | gag | cac | 96 |
| Gly | Leu | Cys | Cys | Thr | Phe | Val | His | Arg | Ala | Arg | Ser | Arg | Tyr | Glu | His | |
| | | | 20 | | | | | 25 | | | | | 30 | | | |
| atc | ccc | ggg | ccg | ccg | cgg | ccc | agt | ttc | ctt | cta | gga | cac | ctc | ccc | tgc | 144 |
| Ile | Pro | Gly | Pro | Pro | Arg | Pro | Ser | Phe | Leu | Leu | Gly | His | Leu | Pro | Cys | |
| | 35 | | | | | 40 | | | | | 45 | | | | | |
| ttt | tgg | aaa | aag | gat | gag | gtt | ggt | ggc | cgt | gtg | ctc | caa | gat | gtg | ttt | 192 |
| Phe | Trp | Lys | Lys | Asp | Glu | Val | Gly | Gly | Arg | Val | Leu | Gln | Asp | Val | Phe | |
| 50 | | | | | 55 | | | | | 60 | | | | | | |
| ttg | gat | tgg | gct | aag | aag | tat | gga | cct | gtt | gtg | cgg | gtc | aac | gtc | ttc | 240 |
| Leu | Asp | Trp | Ala | Lys | Lys | Tyr | Gly | Pro | Val | Val | Arg | Val | Asn | Val | Phe | |
| 65 | | | | | 70 | | | | | 75 | | | | | 80 | |
| cac | aaa | acc | tca | gtc | atc | gtc | acg | agt | cct | gag | tcg | gtt | aag | aag | ttc | 288 |
| His | Lys | Thr | Ser | Val | Ile | Val | Thr | Ser | Pro | Glu | Ser | Val | Lys | Lys | Phe | |
| | | | | 85 | | | | | 90 | | | | | 95 | | |
| ctg | atg | tca | acc | aag | tac | aac | aag | gac | tcc | aag | atg | tac | cgt | gcg | ctc | 336 |
| Leu | Met | Ser | Thr | Lys | Tyr | Asn | Lys | Asp | Ser | Lys | Met | Tyr | Arg | Ala | Leu | |
| | | | 100 | | | | | 105 | | | | | 110 | | | |
| cag | act | gtg | ttt | ggt | gag | aga | ctc | ttc | ggc | caa | ggc | ttg | gtg | tcc | gaa | 384 |
| Gln | Thr | Val | Phe | Gly | Glu | Arg | Leu | Phe | Gly | Gln | Gly | Leu | Val | Ser | Glu | |
| | | 115 | | | | | 120 | | | | | 125 | | | | |
| tgc | aac | tat | gag | cgc | tgg | cac | aag | cag | cgg | aga | gtc | ata | gac | ctg | gcc | 432 |
| Cys | Asn | Tyr | Glu | Arg | Trp | His | Lys | Gln | Arg | Arg | Val | Ile | Asp | Leu | Ala | |
| | 130 | | | | | 135 | | | | | 140 | | | | | |
| ttc | agc | cgg | agc | tcc | ttg | gtt | agc | tta | atg | gaa | aca | ttc | aac | gag | aag | 480 |
| Phe | Ser | Arg | Ser | Ser | Leu | Val | Ser | Leu | Met | Glu | Thr | Phe | Asn | Glu | Lys | |
| 145 | | | | | 150 | | | | | 155 | | | | | 160 | |
| gct | gag | cag | ctg | gtg | gag | att | cta | gaa | gcc | aag | gca | gat | ggg | cag | acc | 528 |
| Ala | Glu | Gln | Leu | Val | Glu | Ile | Leu | Glu | Ala | Lys | Ala | Asp | Gly | Gln | Thr | |
| | | | | 165 | | | | | 170 | | | | | 175 | | |
| cca | gtg | tcc | atg | cag | gac | atg | ctg | acc | tac | acc | gcc | atg | gac | atc | ctg | 576 |
| Pro | Val | Ser | Met | Gln | Asp | Met | Leu | Thr | Tyr | Thr | Ala | Met | Asp | Ile | Leu | |
| | | | 180 | | | | | 185 | | | | | 190 | | | |
| gcc | aag | gca | gct | ttt | ggg | atg | gag | acc | agt | atg | ctg | ctg | ggt | gcc | cag | 624 |
| Ala | Lys | Ala | Ala | Phe | Gly | Met | Glu | Thr | Ser | Met | Leu | Leu | Gly | Ala | Gln | |
| | | 195 | | | | | 200 | | | | | 205 | | | | |
| aag | cct | ctg | tcc | cag | gca | gtg | aaa | ctt | atg | ttg | gag | gga | atc | act | gcg | 672 |
| Lys | Pro | Leu | Ser | Gln | Ala | Val | Lys | Leu | Met | Leu | Glu | Gly | Ile | Thr | Ala | |
| | 210 | | | | | 215 | | | | | 220 | | | | | |
| tcc | cgc | aac | act | ctg | gca | aag | ttc | ctg | cca | ggg | aag | agg | aag | cag | ctc | 720 |
| Ser | Arg | Asn | Thr | Leu | Ala | Lys | Phe | Leu | Pro | Gly | Lys | Arg | Lys | Gln | Leu | |
| 225 | | | | | 230 | | | | | 235 | | | | | 240 | |
| cgg | gag | gtc | cgg | gag | agc | att | cgc | ttc | ctg | cgc | cag | gtg | ggc | agg | gac | 768 |
| Arg | Glu | Val | Arg | Glu | Ser | Ile | Arg | Phe | Leu | Arg | Gln | Val | Gly | Arg | Asp | |
| | | | | 245 | | | | | 250 | | | | | 255 | | |
| tgg | gtc | cag | cgc | cgc | cgg | gaa | gcc | ctg | aag | agg | ggc | gag | gag | gtt | cct | 816 |
| Trp | Val | Gln | Arg | Arg | Arg | Glu | Ala | Leu | Lys | Arg | Gly | Glu | Glu | Val | Pro | |

```
gcc gac atc ctc aca cag att ctg aaa gct gaa gag gga gcc cag gac      864
Ala Asp Ile Leu Thr Gln Ile Leu Lys Ala Glu Glu Gly Ala Gln Asp
        275                 280                 285 gac gag ggt ctg ctg gac aac ttc gtc acc ttc ttt att gct ggt cac      912
Asp Glu Gly Leu Leu Asp Asn Phe Val Thr Phe Phe Ile Ala Gly His
    290                 295                 300 gag acc tct gcc aac cac ttg gcg ttc aca gtg atg gag ctg tct cgc      960
Glu Thr Ser Ala Asn His Leu Ala Phe Thr Val Met Glu Leu Ser Arg
305                 310                 315                 320 cag cca gag atc gtg gca agg ctg cag gcc gag gtg gat gag gtc att     1008
Gln Pro Glu Ile Val Ala Arg Leu Gln Ala Glu Val Asp Glu Val Ile
                325                 330                 335 ggt tct aag agg tac ctg gat ttc gag gac ctg ggg aga ctg cag tac     1056
Gly Ser Lys Arg Tyr Leu Asp Phe Glu Asp Leu Gly Arg Leu Gln Tyr
            340                 345                 350 ctg tcc cag gtc ctc aaa gag tcg ctg agg ctg tac cca cca gca tgg     1104
Leu Ser Gln Val Leu Lys Glu Ser Leu Arg Leu Tyr Pro Pro Ala Trp
        355                 360                 365 ggc acc ttt cgc ctg ctg gaa gag gag acc ttg att gat ggg gtc aga     1152
Gly Thr Phe Arg Leu Leu Glu Glu Glu Thr Leu Ile Asp Gly Val Arg
    370                 375                 380 gtc ccc ggc aac acc ccg ctc ttg ttc agc acc tat gtc atg ggg cgg     1200
Val Pro Gly Asn Thr Pro Leu Leu Phe Ser Thr Tyr Val Met Gly Arg
385                 390                 395                 400 atg gac aca tac ttt gag gac ccg ctg act ttc aac ccc gat cgc ttc     1248
Met Asp Thr Tyr Phe Glu Asp Pro Leu Thr Phe Asn Pro Asp Arg Phe
                405                 410                 415 ggc cct gga gca ccc aag cca cgg ttc acc tac ttc ccc ttc tcc ctg     1296
Gly Pro Gly Ala Pro Lys Pro Arg Phe Thr Tyr Phe Pro Phe Ser Leu
            420                 425                 430 ggc cac cgc tcc tgc atc ggg cag cag ttt gct cag atg gag gtg aag     1344
Gly His Arg Ser Cys Ile Gly Gln Gln Phe Ala Gln Met Glu Val Lys
        435                 440                 445 gtg gtc atg gca aag ctg ctg cag agg ctg gag ttc cgg ctg gtg ccc     1392
Val Val Met Ala Lys Leu Leu Gln Arg Leu Glu Phe Arg Leu Val Pro
    450                 455                 460 ggg cag cgc ttc ggg ctg cag gag cag gcc aca ctc aag cca ctg gac     1440
Gly Gln Arg Phe Gly Leu Gln Glu Gln Ala Thr Leu Lys Pro Leu Asp
465                 470                 475                 480 ccc gtg ctg tgc acc ctg cgg ccc cgc ggc tgg cag ccc gca ccc cca     1488
Pro Val Leu Cys Thr Leu Arg Pro Arg Gly Trp Gln Pro Ala Pro Pro
                485                 490                 495 cca ccc ccc tgc tga                                                  1503
Pro Pro Pro Cys
        500

<210> SEQ ID NO 2
<211> LENGTH: 500
<212> TYPE: PRT
<213> ORGANISM: Homo sapiens

<400> SEQUENCE: 2

Met Ser Pro Gly Leu Leu Leu Leu Gly Ser Ala Val Leu Leu Ala Phe
1               5                   10                  15

Gly Leu Cys Cys Thr Phe Val His Arg Ala Arg Ser Arg Tyr Glu His
            20                  25                  30

Ile Pro Gly Pro Pro Arg Pro Ser Phe Leu Leu Gly His Leu Pro Cys
        35                  40                  45
```

```
Phe Trp Lys Lys Asp Glu Val Gly Gly Arg Val Leu Gln Asp Val Phe
 50                  55                  60

Leu Asp Trp Ala Lys Lys Tyr Gly Pro Val Val Arg Val Asn Val Phe
 65                  70                  75                  80

His Lys Thr Ser Val Ile Val Thr Ser Pro Glu Ser Val Lys Lys Phe
                 85                  90                  95

Leu Met Ser Thr Lys Tyr Asn Lys Asp Ser Lys Met Tyr Arg Ala Leu
                100                 105                 110

Gln Thr Val Phe Gly Glu Arg Leu Phe Gly Gln Gly Leu Val Ser Glu
            115                 120                 125

Cys Asn Tyr Glu Arg Trp His Lys Gln Arg Arg Val Ile Asp Leu Ala
130                 135                 140

Phe Ser Arg Ser Ser Leu Val Ser Leu Met Glu Thr Phe Asn Glu Lys
145                 150                 155                 160

Ala Glu Gln Leu Val Glu Ile Leu Glu Ala Lys Ala Asp Gly Gln Thr
                165                 170                 175

Pro Val Ser Met Gln Asp Met Leu Thr Tyr Thr Ala Met Asp Ile Leu
            180                 185                 190

Ala Lys Ala Ala Phe Gly Met Glu Thr Ser Met Leu Leu Gly Ala Gln
        195                 200                 205

Lys Pro Leu Ser Gln Ala Val Lys Leu Met Leu Glu Gly Ile Thr Ala
210                 215                 220

Ser Arg Asn Thr Leu Ala Lys Phe Leu Pro Gly Lys Arg Lys Gln Leu
225                 230                 235                 240

Arg Glu Val Arg Glu Ser Ile Arg Phe Leu Arg Gln Val Gly Arg Asp
                245                 250                 255

Trp Val Gln Arg Arg Arg Glu Ala Leu Lys Arg Gly Glu Glu Val Pro
            260                 265                 270

Ala Asp Ile Leu Thr Gln Ile Leu Lys Ala Glu Gly Ala Gln Asp
        275                 280                 285

Asp Glu Gly Leu Leu Asp Asn Phe Val Thr Phe Phe Ile Ala Gly His
            290                 295                 300

Glu Thr Ser Ala Asn His Leu Ala Phe Thr Val Met Glu Leu Ser Arg
305                 310                 315                 320

Gln Pro Glu Ile Val Ala Arg Leu Gln Ala Glu Val Asp Glu Val Ile
                325                 330                 335

Gly Ser Lys Arg Tyr Leu Asp Phe Glu Asp Leu Gly Arg Leu Gln Tyr
            340                 345                 350

Leu Ser Gln Val Leu Lys Glu Ser Leu Arg Leu Tyr Pro Pro Ala Trp
        355                 360                 365

Gly Thr Phe Arg Leu Leu Glu Glu Glu Thr Leu Ile Asp Gly Val Arg
    370                 375                 380

Val Pro Gly Asn Thr Pro Leu Leu Phe Ser Thr Tyr Val Met Gly Arg
385                 390                 395                 400

Met Asp Thr Tyr Phe Glu Asp Pro Leu Thr Phe Asn Pro Asp Arg Phe
                405                 410                 415

Gly Pro Gly Ala Pro Lys Pro Arg Phe Thr Tyr Phe Pro Phe Ser Leu
            420                 425                 430

Gly His Arg Ser Cys Ile Gly Gln Gln Phe Ala Gln Met Glu Val Lys
        435                 440                 445

Val Val Met Ala Lys Leu Leu Gln Arg Leu Glu Phe Arg Leu Val Pro
450                 455                 460

Gly Gln Arg Phe Gly Leu Gln Glu Gln Ala Thr Leu Lys Pro Leu Asp
```

-continued

```
            465                 470                 475                 480

Pro Val Leu Cys Thr Leu Arg Pro Arg Gly Trp Gln Pro Ala Pro Pro
                485                 490                 495

Pro Pro Pro Cys
            500
```

EXPRESSION VECTOR FOR CHOLESTEROL 24-HYDROLASE IN THERAPY OF POLYGLUTAMINE REPEAT SPINOCEREBELLAR ATAXIAS

RELATED APPLICATIONS

This application is a U.S. National Stage Entry of PCT/EP2018/052199, which claims priority to European Patent Application number 17305100, filed Jan. 30, 2017.

SEQUENCE LISTING

The instant application contains a Sequence Listing which has been submitted electronically in ASCII format and is hereby incorporated by reference in its entirety. Said ASCII copy, created on Dec. 1, 2021, is named 046192-098270US-PX_SL.txt and is 12,334 bytes in size.

The present invention relates to treatment of polyglutamine repeat spinocerebellar ataxias.

BACKGROUND OF THE INVENTION

Spinocerebellar ataxias (SCA) belong to the group of neurodegenerative disorders characterized by slowly progressive in-coordination of gait and troubles of balance, often associated with poor coordination of hands, speech and eye movements. Spinocerebellar ataxias result in unsteady and clumsy motion of the body due to a failure of the fine coordination of muscle movements.

Spinocerebellar ataxias are associated with progressive disappearance of part of the nervous system cells located in the cerebellum, leading to atrophy of the cerebellum. Spinocerebellar ataxias are genetic disorders associated with different gene alterations. Numerous types of spinocerebellar ataxias are now known, for which specific genetic information is available. The first ataxia gene was identified in 1993 for a dominantly inherited type, and was called "Spinocerebellar ataxia type 1" (SCA1). Subsequently, as additional dominant genes were found, they were called SCA2, SCA3, etc. Usually, the "type number of SCA refers to the order in which the gene was found. At this time, there are at least 29 different gene mutations which have been found.

The most common alteration consists on an excessive repetition of the trinucleotide cytosine-adenine-guanine (CAG) in some genes located in different chromosomes. Those ataxias with poly CAG expansions are referred to as polyglutamine repeat spinocerebellar ataxias. The excessive repetition of CAG in a gene may lead to the repetition of glutamine in the protein encoded by said gene, producing abnormal protein.

As an example, Spinocerebellar ataxia type 3 (SCA3) also called Machado-Joseph disease (MJD) is a progressive autosomal dominant inherited adult-onset neurodegenerative disorder (Dun et al., 1996), caused by a CAG-repeat expansion in the coding region of the MJD1 gene, which results in an abnormally expanded polyglutamine (PolyQ) tract in the coding region of the ataxin-3 (ATXN3) gene (Kawaguchi et al., 1994). It confers a toxic gain of function to the expanded ATXN3 protein which abnormally accumulates in neuronal cells, thus promoting the formation of insoluble intranuclear inclusions (Orr and Zoghbi, 2007; Schols et al., 2004). SCA3 is clinically revealed as a range of progressive cerebellar dysfunctions unpredictably associated with degeneration of the striatum, substantia nigra and cranial nerve motor nuclei (Alves et al., 2008b; Durr et al., 1996; Klockgether et al., 1998; Rub et al., 2008), therefore resulting in a broad spectrum of symptoms such as ataxia, lack of motor coordination, postural instability, parkinsonism, pyramidal signs and neuropathy among other symptoms (Burk et al., 1999; Rub et al., 2006; Schols et al., 1997; Schols et al., 2004). A spinal cord involvement has also been described (Lukas et al., 2008).

The general prevalence of SCA is of 1 for 125.000, but in some part of the world, such as in the Azorean islands, the prevalence of SCA3 is up to 1 for 140.

Up to now, there is no known cure for SCA. Treatments are generally limited to softening symptoms. There is thus an acute need to develop new strategies for therapy in SCA in general and polyglutamine repeat spinocerebellar ataxias (PolyQ SCA) in particular.

SUMMARY OF THE INVENTION

The inventors have shown a dysfunction of the cholesterol metabolism in patients with a PolyQ SCA. Based on this discovery, the inventors successfully studied the possibility to address the modulation of the cholesterol metabolism pathway as a therapeutic strategy to counteract PolyQ SCA, by use of a vector comprising cholesterol 24-hydroxylase encoding nucleic acid that expresses cholesterol 24-hydroxylase in the target cells.

It is therefore an object of the present invention to provide a vector for use in the treatment of a polyglutamine repeat spinocerebellar ataxia, which vector comprises cholesterol 24-hydroxylase encoding nucleic acid.

In an embodiment, the Polyglutamine repeat spinocerebellar ataxia selected from the group of Spinocerebellar ataxia type 1 (SCA1), Spinocerebellar ataxia type 2 (SCA2), Spinocerebellar ataxia type 3 (SCA3), Spinocerebellar ataxia type 6 (SCA6), Spinocerebellar ataxia type 7 (SCA7) and Spinocerebellar ataxia type 17 (SCA17).

In an embodiment, the vector comprises a nucleic acid sequence that encodes the amino acid sequence SEQ ID No 2. Alternatively, the vector comprises the nucleic acid sequence SEQ ID No 1.

In an embodiment, the vector is selected from the group of adenovirus, lentivirus, retrovirus, herpes-virus and Adeno-Associated Virus (AAV) vectors, preferably an AAV vector, more preferably an AAV9 or AAV10 (AAVrh.10) vector, even more preferably an AAVrh.10.

In an embodiment, the vector is to be administered directly into the brain of the patient, preferably to cerebellum, striatum, brainstem, frontotemporal lobes and/or visual cortex, more preferably to cerebellum. Alternatively or in addition, the vector is to be administered into the spinal cord of the patient.

It is another object of the invention to provide a pharmaceutical composition for use in the treatment of polyglutamine repeat spinocerebellar ataxias, which comprises a vector comprising cholesterol 24-hydroxylase encoding nucleic acid.

FIGURES

The patent or application file contains at least one drawing executed in color. Copies of this patent or patent application publication with color drawing(s) will be provided by the Office upon request and payment of the necessary fee.

Figure 2:
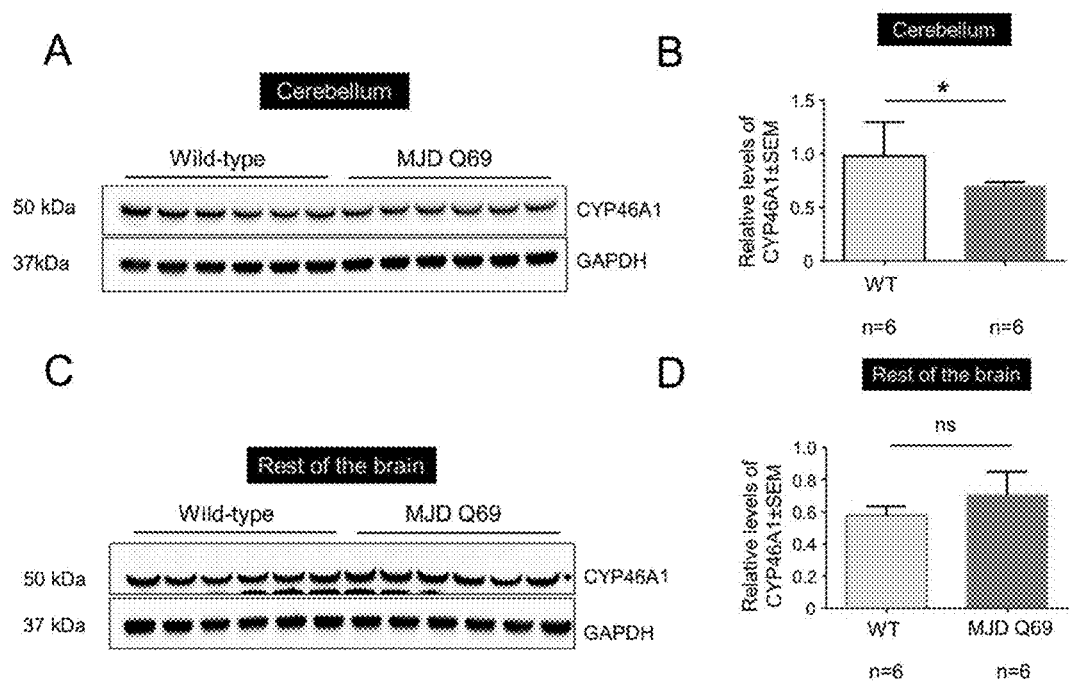
Figure 3:
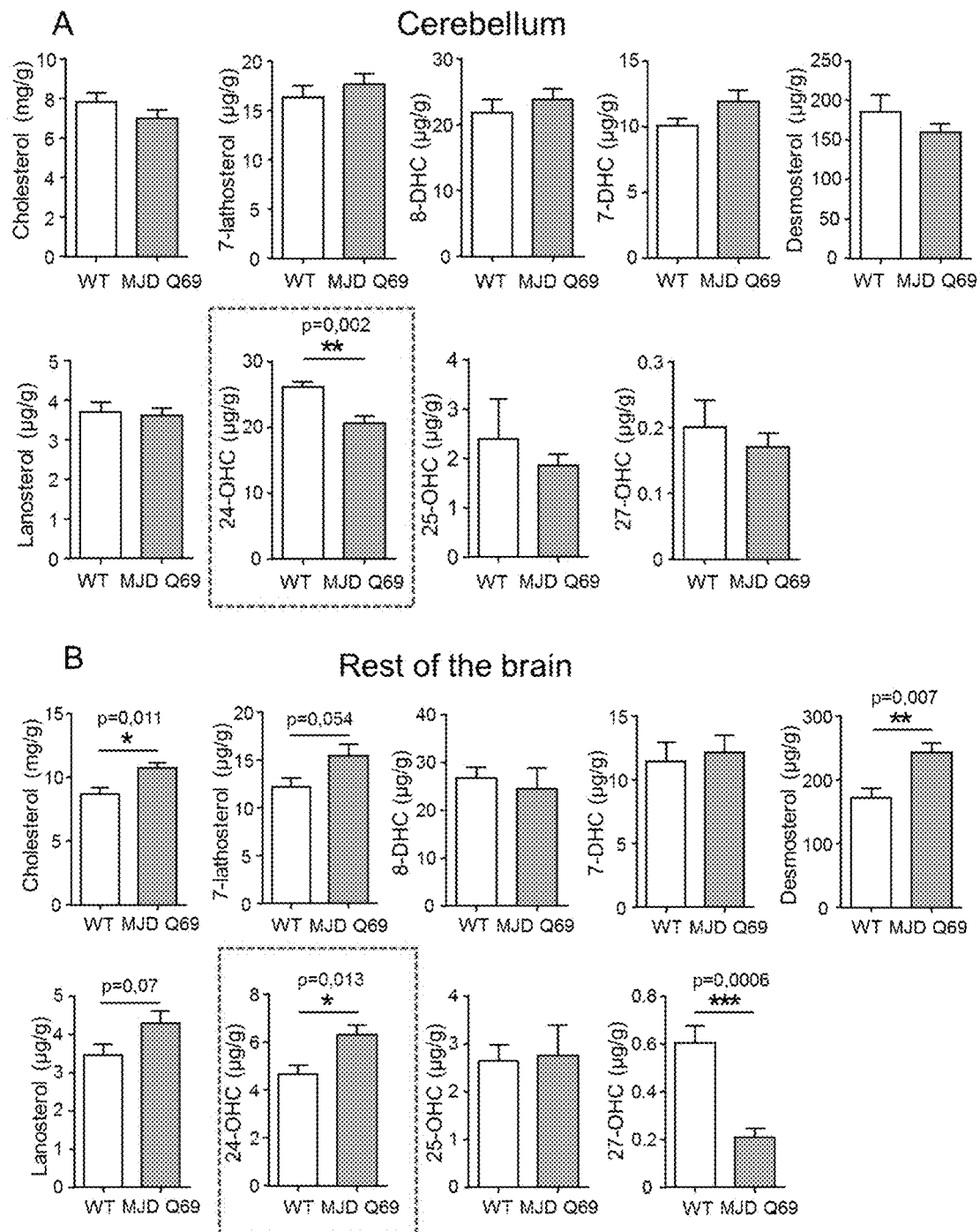
Figure 4:
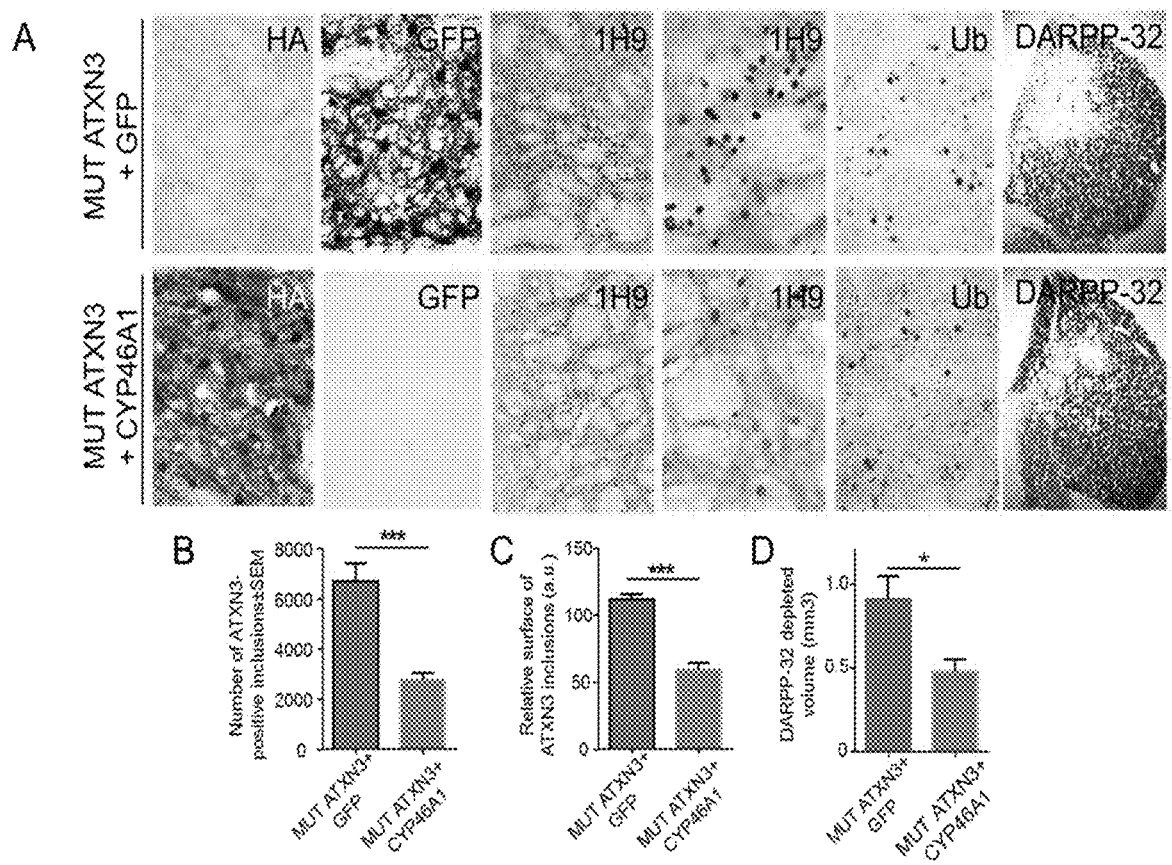

FIG. 1—Representative western-blot showing the levels of the HA tag in the cerebellum and "rest of the brain" of MJD transgenic mice (n=6) vs. wild-type controls (n=6). Frozen biopsies from six MJD transgenic mice expressing the N-terminal truncated human ATXN3, with 69 CAG repeats and six age-matched control littermates were used;

FIG. 2—Representative western-blots showing the levels of CYP46A1 protein in the brain of MJD mice (n=6) and wild-type controls (n=6). Optical densitometry revealing 24.3% reduction in CYP46A1 protein levels (Mann-Whitney test; p=0.026) in cerebellar biopsies from MJD mice relatively to control littermates (A and B). No statistical significant differences were found in biopsies from the "rest of the brain" in MJD mice and controls (Mann-Whitney test; p=0.13) (C and D);

FIG. 3—Quantitative measurements of both sterols and oxysterols by gas-chromatography mass spectrometry (GC/MS) in cerebellar extracts and also biopsies from the "rest of the brain" from MJD Q69 mice (n=6) and age-matched littermates (n=6), showing impairments in the cholesterol metabolism pathway in MJD mice relatively to control littermates;

FIG. 4—AAV-based CYP46A1 overexpression alleviates neuropathology in an LV-based mouse model of MJD, 2 months post-injection. A) Representative immunohistochemistry detecting the presence of the HA tag in AAVrh.10-CYP46A1-injected LV-MJD mice but not in the control group injected with AAVrh.10-GFP; in mice injected with AAVrh.10-GFP, widespread GFP immunoreactivity is detected in the mouse striatum whereas no HA signal is detected. Immunohistochemistry and quantitative analysis for mutant ataxin-3-positive inclusions (revealed with the 1H9 antibody) (A) revealed a statistically significant decrease (~59%) in the number of ataxin-3-positive inclusions (2751±267.8; n=8) compared to the control group (GFP-co-injected mice; 6684±717.2 inclusions; n=8; Student's T test, P=0.0002) (B). A statistically significant decrease in the size of inclusions (~47%) in AAVrh.10-CYP46A1 treated LV-MJD mice (59.29±4.67 arbitrary units (a.u.); n=8) compared to LV-MJD mice injected with the control AAVrh.10-GFP (111.4±3.96 a.u.; n=8; Student's T test, P<0.0001) was observed (C). Anti-ubiquitin staining that demonstrated a reduction in the number of ubiquitinated inclusions (qualitative analysis) in LV-MJD mice injected with AAVrh.10-CYP46A1 relatively to LV-MJD mice injected with control AAVrh.10-GFP (A). CYP46A1 overexpression led to a statistically significant reduction (~48%) of DARPP-32 depleted region (0.48±0.77 mm$^3$; n=8) relatively to LV-MJD mice injected with control AAVrh.10-GFP (0.91±0.14 mm$^3$; n=8) Student's T test; P=0.015).

Figure 5:
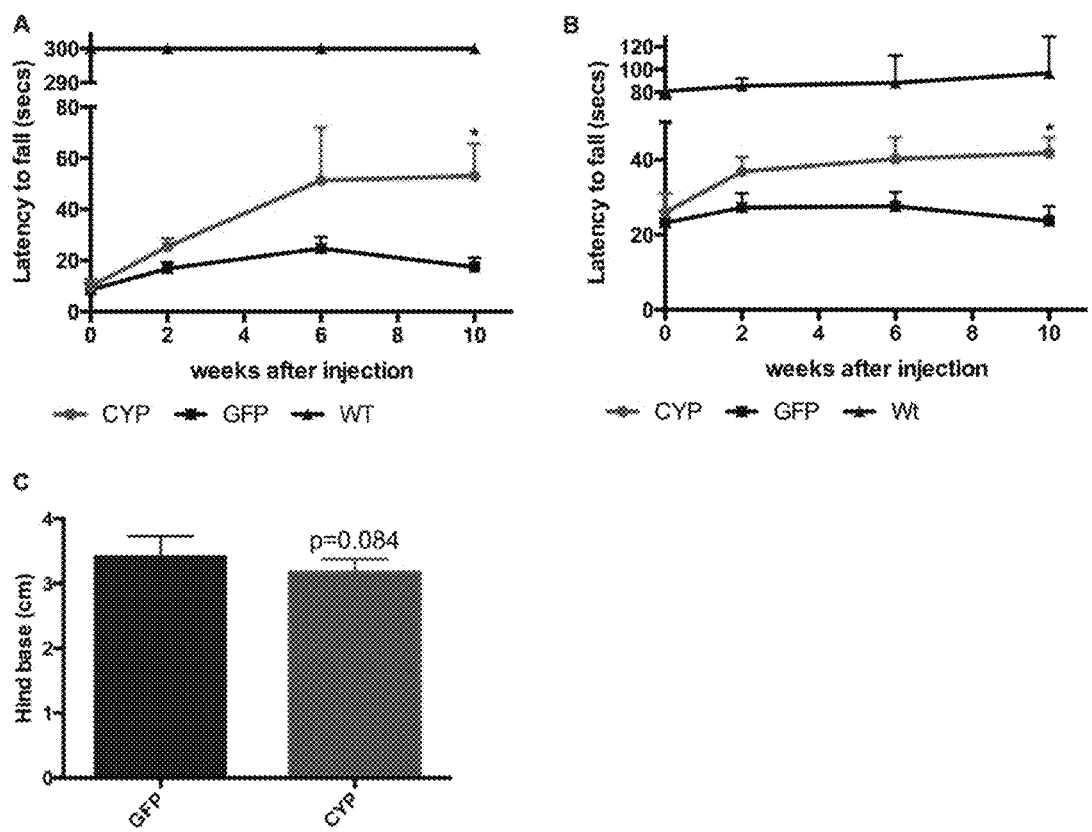

FIG. 5: Effect of AAV-CYP46A1 expression in the motor coordination impairments of MJD-transgenic mice. Non injected wild-type mice (WT) and MJD-transgenic mice injected with AAV10 encoding for CYP46A1 (CYP) or GFP (GFP) were assessed for motor coordination performance over 10 weeks. Mice were tested for A) rotarod at constant velocity, B) accelerated rotarod and C) hind base test (footprinting test). A significant improvement of the motor performance in the transgenic MJD mice treated with CYP46A1 as compared to the control mice (GFP) was observed. Data are presented as mean±SEM. Two-way ANOVA analysis with Bonferroni post-test; *p<0.05. CYP: n=10; GFP: n=9; WT: n=4.

Figure 6:
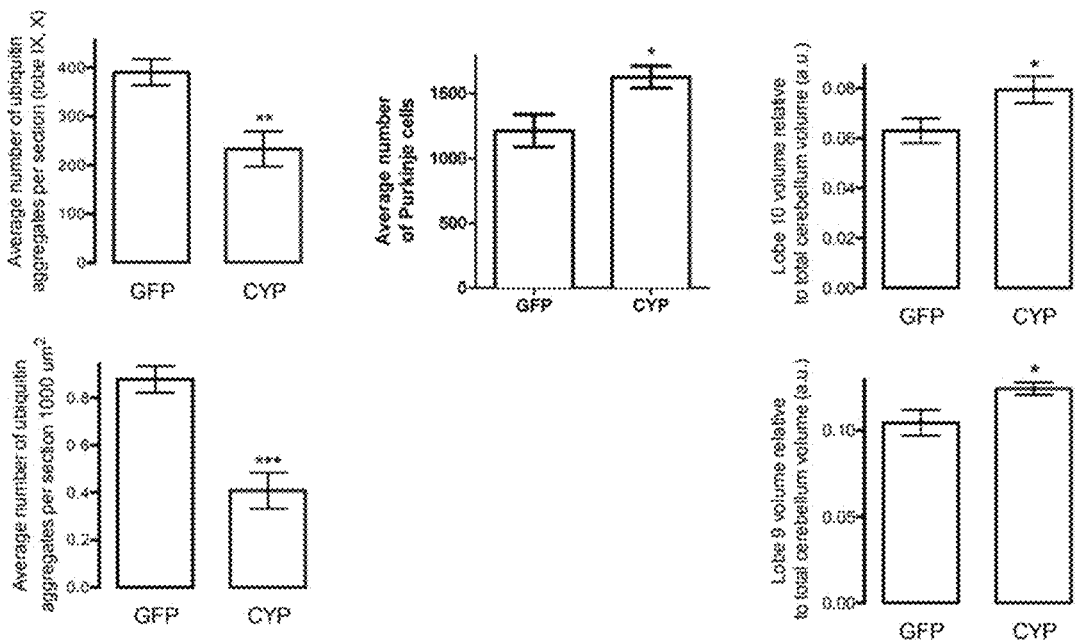

FIG. 6: AAV-CYP46A1 overexpression decreases aggregation and mitigates Purkinje cell loss in the cerebellum of MJD-transgenic mice. Immunohistochemistry in MJD-transgenic mice injected with AAV10 encoding for CYP46A1 (CYP) or GFP (GFP) demonstrates a decrease of ubiquitinated aggregates (A). AAV10-CYP46A1 injected MJD transgenic mice display increased average number of Purkinje cells (B) and increased cerebellar volume (C) relatively to MJD transgenic mice treated with the control vector (AAV10-GFP).

Figure 7:
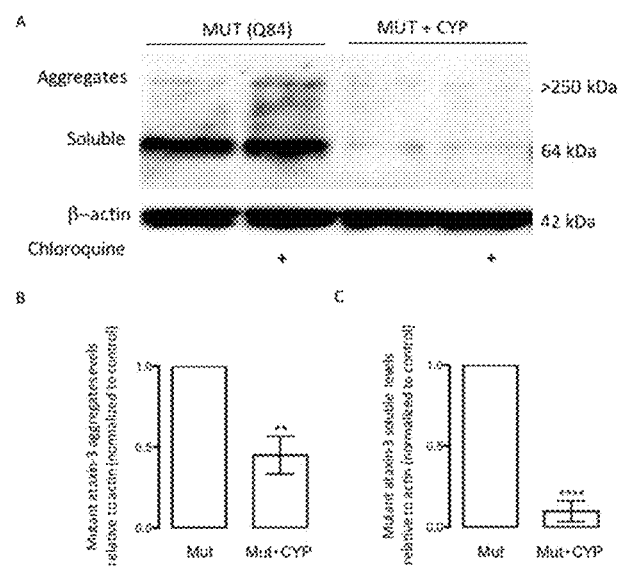

FIG. 7: Representative western-blot depicting the levels of mutant ATXN3 upon CYP46A1 overexpression in Neuro2A cells (A). Optical densitometry analysis revealed a 66% and 90% reduction of mutant ATXN3 aggregates (B) and soluble levels (C), respectively, upon CYP46A1 overexpression (Student t-test, p=0.0033; n=4).

Figure 8:
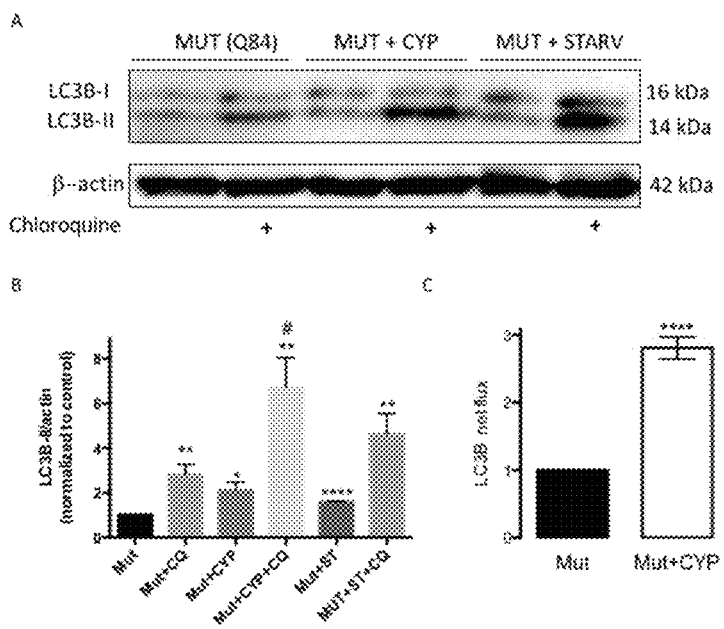

FIG. 8: Representative western-blot depicting the levels of autophagy marker LC3B-II upon CYP46A1 overexpression in Neuro2A cells (A). Optical densitometry analysis revealed an increase in autophagy upon CYP46A1 overexpression highlighted by an increase in the LC3B-II compared to controls conditions, both with and without autophagy inhibitor chloroquine (B). Moreover, CYP46A1 overexpression induced an increase in LC3B-II net flux compared to control levels, suggesting an activation of autophagic flux (C). (*P<0.05, P<0.01; *P<0.001; ****P<0.0001; Unpaired Student's t-test; n=4).

DETAILED DESCRIPTION OF THE INVENTION

The inventors demonstrated that delivering a vector expressing a CYP46A1 gene into the brain of a mouse model of Polyglutamine repeat spinocerebellar ataxia, resulted in a significant decrease of neuronal dysfunction, and more particularly of cerebellum attacks.

On this basis, the inventors provide a viral vector for the treatment of Polyglutamine repeat spinocerebellar ataxias, wherein the vector expresses CYP46A1 in cells of the central nervous system.

Polyglutamine Repeat Spinocerebellar Ataxias

The present invention specifically relates to treatment of polyglutamine repeat spinocerebellar ataxias, which are caused when a disease-associated protein (i.e., ataxin-1, ataxin-3, etc.) contains an abnormal number of repeats of glutamine residues, termed a polyQ or a "CAG trinucleotide repeat" disease.

In the context of the invention, the terms "treatment", "treat" or "treating" are used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

As used herein, the term "subject" or "patient" refers to an animal, preferably to a mammal, even more preferably to a human, including adult and child. However, the term "subject" can also refer to non-human animals, in particular mammals such as mouse, and non-human primates.

The present invention relates preferably to a Polyglutamine repeat spinocerebellar ataxia selected from the group of Spinocerebellar ataxia type 1 (SCA1), Spinocerebellar ataxia type 2 (SCA2), Spinocerebellar ataxia type 3 (SCA3), Spinocerebellar ataxia type 6 (SCA6), Spinocerebellar ataxia type 7 (SCA7) and Spinocerebellar ataxia type 17 (SCA17).

SCA1, or SCA type 1, is characterized by abnormal CAG repeats in the gene encoding Ataxin 1 protein (ATXN1). This elongation is variable in length. The shortest repeat length shown to cause SCA1 is 39 uninterrupted CAG triplets, and the longest observed to date contained 83 repeats. Longer repeat tracts are correlated with earlier age of onset and faster progression. Mutant ATXN1 protein spontaneously misfolds and forms aggregates in the nucleus of Purkinje neurons.

SCA2, or SCA type 2, is characterized by abnormal CAG repeats in the coding region of the ATXN2 gene producing an elongated polyglutamine tract in the corresponding protein. The expanded repeats are variable in size and unstable, usually increasing in size when transmitted to successive generation. The locus has been mapped to chromosome 12, and it has been determined that the disease allele usually contains 34 to 52 CAG repeats, but can contain as few as 32 or more than 100.

SCA3, or SCA type 3, also called Machado-Joseph disease (MJD), is characterized by abnormal CAG repeats in the gene encoding the Ataxin 3 protein (A TXN3). The expansion of these repeats from the normal 13-36 to the abnormal 68-79 is the cause of MJD. There is an inverse correlation between the age of onset and CAG repeat numbers.

SCA6, or SCA type 6, is characterized by an insertion that extends the coding region of CACNA1A gene, that encodes the $Ca_v2.1$ P/Q voltage-dependent calcium channel, to include from 4-16 to 21-28 CAG repeats.

SCAT, or SCA type 7, is characterized by abnormal CAG repeats in the coding region of the ATXN7 gene, producing an elongated polyglutamine tract in the corresponding protein (ATXN7).

SCA17, or SCA type 17, is characterized by abnormal CAG repetitions in the coding region of the gene encoding the TATA-binding protein (TBP). TBP is characterized by a long string of glutamines in the N-terminus of the protein. This region modulates the DNA binding activity of the C-terminus, and modulation of DNA-binding affects the rate of transcription complex formation and initiation of transcription. The expand of the number of CAG repeats thus increases the length of the glutamine string and thereby affect the DNA binding activity of the TBP.

The CYP46A1 Sequences

A first object of the invention relates to a vector for use in the treatment of a PolyQ SCA, which comprises the full sequence of cholesterol 24-hydroxylase encoding nucleic acid.

As used herein, the term "gene" refers to a polynucleotide containing at least one open reading frame that is capable of encoding a particular polypeptide or protein after being transcribed or translated.

As used herein, the terms "coding sequence" or "a sequence which encodes a particular protein", denotes a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

The CYP46A1 gene encodes cholesterol 24-hydroxylase. This enzyme is a member of the cytochrome P450 superfamily of enzymes. The enzyme converts cholesterol into 24S-hydroxycholesterol (24S—OH-Chol) that can dynamically cross the BBB, accomplishing peripheral circulation to be evacuated out of the body (Bjorkhem et al., 1998), thus maintaining cholesterol homeostasis. A cDNA sequence for CYP46A1 is disclosed in Genbank Access Number AF094480 (SEQ ID NO:1). The amino acid sequence is shown in SEQ ID NO:2.

The invention makes use of a nucleic acid construct comprising sequence SEQ ID NO:1 or a variant thereof for the treatment of a Polyglutamine repeat spinocerebellar ataxia.

The variants include, for instance, naturally-occurring variants due to allelic variations between individuals (e.g., polymorphisms), alternative splicing forms, etc. The term variant also includes CYP46A1 gene sequences from other sources or organisms. Variants are preferably substantially homologous to SEQ ID NO:1, i.e., exhibit a nucleotide sequence identity of typically at least about 75%, preferably at least about 85%, more preferably at least about 90%, more preferably at least about 95% with SEQ ID NO:1. Variants of a CYP46A1 gene also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

Non-Viral Vectors

In an embodiment, the vector use according to the present invention is a non-viral vector. Typically, the non-viral vector may be a plasmid encoding CYP46A1. This plasmid can be administered directly or through a liposome, an exosome or a nanoparticle.

Viral Vectors

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "gene transfer" or "gene delivery" refer to methods or systems for reliably inserting foreign DNA into host cells. Such methods can result in transient expression of non-integrated transferred DNA, extrachromosomal replication and expression of transferred replicons (e. g; episomes), or integration of transferred genetic material into the genomic DNA of host cells.

Examples of viral vector include adenovirus, lentivirus, retrovirus, herpes-virus and Adeno-Associated virus (AAV) vectors.

Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. Nos. 5,882,877, 6,013,516, 4,861, 719, 5,278,056 and WO94/19478.

In a preferred embodiment, adeno-associated viral (AAV) vectors are employed.

By an "AAV vector" is meant a vector derived from an adeno-associated virus serotype, including without limitation, AAV1, AAV2, AAV3, AAV4, AAV5, AAV6, AAV7, AAV8, AAV9, AAV10, such as AAVrh.10, AAV-PHP.B (Benjamin E. Deverman et al., 2016), etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e. g., functional ITRs) of the virus. The ITRs need not be the wild-type nucleotide sequences, and may be altered, e. g, by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e. the CYP46A1 gene) and a transcriptional termination region. Two copies of the DNA of interest can be included, as a self-complementary construct (McCarty et al., 2001).

In a more preferred embodiment, the AAV vector is an AAV9 or AAV10 (AAVrh.10) vector, or vector derived from one of these serotypes. In a most preferred embodiment, the AAV vector is an AAVrh.10 vector.

The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. (See, e. g., Kotin, 1994; Berns, K I "Parvoviridae and their Replication" in Fundamental Virology, 2nd Edition, (B. N. Fields and D. M. Knipe, eds.) for the AAV-2 sequence. As used herein, an "AAV ITR" does not necessarily comprise the wild-type nucleotide sequence, but may be altered, e. g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, etc. Furthermore, 5' and 3' ITRs which flank a selected nucleotide sequence in an AAV vector need not necessarily be identical or derived from the same AAV serotype or isolate, so long as they function as intended, i. e., to allow for excision and rescue of the sequence of interest from a host cell genome or vector, and to allow integration of the heterologous sequence into the recipient cell genome when AAV Rep gene products are present in the cell.

Particularly preferred are vectors derived from AAV serotypes having tropism for and high transduction efficiencies in cells of the mammalian central nervous system (CNS), particularly neurons. A review and comparison of transduction efficiencies of different serotypes is provided in Davidson et al., 2000. In one preferred example, AAV2 based vectors have been shown to direct long-term expression of transgenes in CNS, preferably transducing neurons. In other non-limiting examples, preferred vectors include vectors derived from AAV4 and AAV5 serotypes, which have also been shown to transduce cells of the CNS (Davidson et al, supra). In particular, the vector may be an AAV vector comprising a genome derived from AAV5 (in particular the ITRs are AAV5 ITRs) and a capsid derived from AAV5. In another non-limiting example, preferred vectors include vectors obtained by use of cre-recombinantion-based AAV targeted evolution (CREATE) like AAV-PHP.B.

In a particular embodiment of the invention, the vector is a pseudotyped AAV vector. Specifically, a pseudotyped AAV vector comprises an AAV genome derived from a first AAV serotype and a capsid derived from a second AAV serotype. Preferably, the genome of the AAV vector is derived from AAV2. Furthermore, the capsid is preferably derived from AAV5. Specific non-limiting examples of pseudotyped AAV vectors include an AAV vector comprising a genome derived from AAV2 in a capsid derived from AAV5, an AAV vector comprising a genome derived from AAV2 in a capsid derived from AAVrh.10, etc.

The selected nucleotide sequence is operably linked to control elements that direct the transcription or expression thereof in the subject in vivo. Such control elements can comprise control sequences normally associated with the selected gene. In particular, such control elements may include the promoter of the CYP46A1 gene, in particular the promoter of the human CYP46A1 gene (Ohyama Y et al., 2006)

Alternatively, heterologous control sequences can be employed. Useful heterologous control sequences generally include those derived from sequences encoding mammalian or viral genes. Examples include, but are not limited to, the phophoglycerate kinase (PGK) promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e. g., Stratagene (San Diego, CA). For purposes of the present invention, both heterologous promoters and other control elements, such as CNS-specific and inducible promoters, enhancers and the like, will be of particular use.

Examples of heterologous promoters include the CMV promoter. Examples of CNS specific promoters include those isolated from the genes from myelin basic protein (MBP), glial fibrillary acid protein (GFAP), synapsins (e.g. human sysnapsin 1 gene promoter), and neuron specific enolase (NSE).

Examples of inducible promoters include DNA responsive elements for ecdysone, tetracycline, hypoxia andaufin.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e. g., U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin,1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e. g; U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. (See, e. g., Edge, 1981; Nambair et al., 1984; Jay et al., 1984). In order to produce rAAV virions, an AAV expression vector is introduced into a suitable host cell using known techniques, such as by transfection. A number of transfection techniques are generally known in the art. (See, e. g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981). Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Felgner et al., 1987), and nucleic acid delivery using high-velocity microprojectiles (Klein et al., 1987).

For instance, a preferred viral vector, such as the AAVrh.10, comprises, in addition to a cholesterol 24-hydroxylase encoding nucleic acid sequence, the backbone of AAV vector with ITR derived from AAV-2, the promoter, such as the mouse PGK (phosphoglycerate kinase) gene or the cytomegalovirus/β-actin hybrid promoter (CAG) consisting of the enhancer from the cytomegalovirus immediate gene, the promoter, splice donor and intron from the chicken β-actin gene, the splice acceptor from rabbit β-globin, or any neuronal promoter such as the promoter of Dopamine-1 receptor or Dopamine-2 receptor with or without the wild-type or mutant form of woodchuck hepatitis virus post-transcriptional regulatory element (WPRE).

Delivery of the Vectors

A method of treatment of polyglutamine repeat spinocerebellar ataxia is disclosed, which method comprises administering a vector comprising cholesterol 24-hydroxylase encoding nucleic acid to a patient in need thereof. The vector may be delivered directly into the brain of the subject or by intravascular, intravenous, intranasal, intraventricular or intrathecal injection.

In a particular embodiment, it is provided a method for treating a Polyglutamine repeat spinocerebellar ataxia (PolyQ SCA) in a subject, said method comprising:
(a) providing a vector as defined above, which comprises a cholesterol 24-hydroxylase encoding nucleic acid; and
(b) delivering the vector to the brain of the subject, whereby said vector transduces cells in the brain, and whereby cholesterol 24-hydroxylase is expressed by the transduced cells at a therapeutically effective level.

Advantageously, the vector is a viral vector, more advantageously an AAV vector, even advantageously an AAV 9 or AAV10 vector, such as AAVrh.10.

In a particular embodiment, the vector is delivered to cerebellum, striatum, brainstem, frontotemporal lobes, and/or visual cortex, spinal cord, preferably at least to cerebellum. In a particular embodiment, the vector is delivered exclusively to cerebellum.

Methods of delivery, or administration, of viral vectors to neurons and/or astrocytes and/or oligodendrocytes and/or microglia include generally any method suitable for delivery vectors to said cells, directly or through hematopoietic cells transduction, such that at least a portion of cells of a selected synaptically connected cell population is transduced. The vector may be delivered to any cells of the central nervous system, cells of the peripheral nervous system, or both. Preferably, the vector is delivered to cells of the brain. Generally, the vector is delivered to the cells of the brain, including for example cells of brainstem (medulla, pons, and midbrain), cerebellum, susbtantia nigra, striatum (caudate nucleus and putamen), frontotemporal lobes, visual cortex, spinal cord or combinations thereof, or preferably any suitable subpopulation thereof.

To deliver the vector specifically to a particular region and to a particular population of cells of the brain, the vector may be administered by stereotaxic microinjection. For example, patients have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of vector injection) and trajectory. The software directly translates the trajectory into 3 dimensional coordinates appropriate for the stereotactic frame. Burr holes are drilled above the entry site and the stereotactic apparatus positioned with the needle implanted at the given depth. The vector is then injected at the target sites, eventually mixed with a contrast agent. Since the vector integrates into the target cells, rather than producing viral particles, the subsequent spread of the vector is minor, and mainly a function of passive diffusion from the site of injection and of course the desired trans-synaptic transport, prior to integration. The degree of diffusion may be controlled by adjusting the ratio of vector to fluid carrier.

Additional routes of administration may also comprise local application of the vector under direct visualization, e. g., superficial cortical application, intranasal application, or other non-stereotactic application.

The target cells of the vectors of the present invention are cells of the brain of a subject afflicted with PolyQ SCA, preferably neural cells. Preferably the subject is a human being, generally an adult but may be a child or an infant.

However the invention encompasses delivering the vector to biological models of the disease. In that case, the biological model may be any mammal at any stage of development at the time of delivery, e. g., embryonic, foetal, infantile, juvenile or adult, preferably it is an adult. Furthermore, the target cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e. g. zebrafish model system).

Preferably, the method of the invention comprises intracerebral administration, through stereotaxic injections. However, other known delivery methods may also be adapted in accordance with the invention. For example, for a more widespread distribution of the vector across the brain, it may be injected into the cerebrospinal fluid, e. g., by lumbar puncture, cisterna magna or ventricular puncture. To direct the vector to the brain, it may be injected into the spinal cord or into the peripheral ganglia, or the flesh (subcutaneously or intramuscularly) of the body part of interest. In certain situations the vector can be administered via an intravascular approach. For example, the vector can be administered intra-arterially (carotid) in situations where the blood-brain barrier is disturbed. Moreover, for more global delivery, the vector can be administered during the "opening" of the blood-brain barrier achieved by infusion of hypertonic solutions including mannitol or ultra-sound local delivery.

The vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes or exosomes.

The preferred doses and regimen may be determined by a physician, and depend on the age, sex, weight, of the subject, and the stage of the disease. As an example, for delivery of cholesterol 24-hydroxylase using a viral expression vector, each unit dosage of cholesterol 24-hydroxylase expressing vector may comprise 2.5 to 100 µl of a composition including a viral expression vector in a pharmaceutically acceptable fluid and which provides from $10^{10}$ up to $10^{15}$ cholesterol 24-hydroxylase expressing viral particles per ml of composition.

Pharmaceutical Composition

A further object of the invention concerns a pharmaceutical composition for use in the treatment of PolyQ SCAs, which comprises a therapeutically effective amount of a vector according to the invention.

By a "therapeutically effective amount" is meant a sufficient amount of the vector of the invention to treat PolyQ SCAs at a reasonable benefit/risk ratio applicable to any medical treatment.

It will be understood that the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range per adult per day. The therapeutically effective amount of the vector according to the invention that should be administered, as well as the dosage for the treatment of a pathological condition with the number of viral or non-viral particles and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the vector according to the invention may be in any form that is suitable for intramuscular, intracerebral, intranasal, intrathecal, intraventricular or intravenous administration. In the pharmaceutical compositions of the present invention for intramuscular, intranasal, intravenous, intracerebral, intrathecal or intraventicular administration, the active principle, alone or in combination with another active principle, can be administered in a unit administration form, as a mixture with conventional pharmaceutical supports, to animals and human beings.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of sterile injectable solutions.

Upon formulation, solutions will be administered in a manner compatible with the dosage formulation and in such amount as is therapeutically effective. The formulations are easily administered in a variety of dosage forms, such as the type of injectable solutions, but drug release capsules and the like can also be employed.

Multiple Doses Can Also Be Administered.

The invention will be further illustrated by the following example. However, this example and the accompanying figures should not be interpreted in any way as limiting the scope of the present invention.

Example

The therapeutic benefits of CYP46A1 overexpression was evaluated in two mouse models of PolyQ spinocerebellar ataxia: a lentiviral-based animal model of MJD/SCA3 and a transgenic mouse model of PolyQ with severe established pathology.

Materials and Methods

Animals

Two-months aged C57Bl/6 mice (n=8) were obtained by Charles River (Spain) and three-month old transgenic MJD Q69 mice (n=6) and age-matched wild-type littermates (n=6) (Oue et al., 2009; Torashima et al., 2008) were used. MJD transgenic mice (C57BL/6 background) overexpress the N-terminal-truncated human ATXN3, containing 69 CAG repeats and an N-terminal haemagglutinin (HA) tag epitope, driven specifically in cerebellar Purkinje cells by the L7 promoter (Oue et al., 2009). This truncated ATXN3 fragment lacks N-terminal 286 amino-acids that contain the ubiquitin-proteasome domain (Josephin domain) and ubiquitin interaction motifs (UIMs). Therefore, the truncated protein consists of a 69 polyQ tract with only 4 and 42 amino-acids at its N-terminus and C-terminus, respectively. A colony of these transgenic mice was established at the Centre for Neuroscience and Cell Biology of Coimbra. Mice were housed in a temperature-controlled room and maintained on a 12 h light/dark cycle. Food and water were available ad libitum. The experiments were carried out in accordance with the European Community Council directive (2010/63/EU) for the care and use of laboratory animals.

Lentiviral Vectors Production

Lentiviral vectors encoding human mutant ataxin-3 (LV-PGK-Atx-3 72Q) were produced in HEK293T cell line with a four-plasmid system, as previously described (Alves et al., 2008b). Lentiviral particles were re-suspended in 1% BSA in sterile PBS. The viral particle content of batches was evaluated by assessing HIV-1 p24 antigen levels by ELISA (Retro Tek, Gentaur, Paris, France). Concentrated viral stocks were stored at −80° C. until use.

AAV Plasmid Design and Vector Production

AAV vectors were produced and purified by Atlantic Gene therapies (INSERM U1089, Nantes, France). Vector production has been described elsewhere (Hudry et al., 2010). The viral constructs for AAVrh.10-GFP and AAVrh.10-CYP46A1 contained the expression cassette consisting of either the Gfp or the human Cyp46a1genes, driven by a CMV early enhancer/chicken β-actin (CAG) synthetic promoter (CAG) surrounded by inverted terminal repeats (ITR) sequences of AAV2. The AAVrh.10-CAG-GFP vector was also generated and was used as control.

Stereotactical Injections in the Mouses Brain

Five-week-old mice were anaesthetized with avertin (14 ml g/1 and 250 mg kg/1 intraperitoneally). Four each animal, 400,000 ng of p24 antigen of lentiviral vectors encoding ATXN3 72Q (MUT ATXN3) and $3.10^{12}$ vg/mL of AAVrh.10 encoding CYP46A1 or the Green Fluorescent protein (GFP; control) in a final volume of 2 µl were stereotactically co-injected (0.2 µl/min) into the striatum in the following coordinates: anteroposterior: +0.6 mm, lateral: ±1.8 mm, ventral: −3.3 mm and tooth bar: 0. After injection, the syringe needle was left in place for an additional 5 min before being slowly raised. The skin was closed using a 6-0 Prolene® suture (Ethicon, Johnson and Johnson, Brussels, Belgium). For cerebellar injections, 6 week-old transgenic MJD Q69 mice (n=25) and age-matched wild-type littermates (n=10) were injected into the cerebellar vermis with AAVrh10-CYP46A1 or AAVrh10-GFP (2 µl; $4.10^9$ vg) at 0.25 ul/min at the coordinates: −1.6 mm rostral to lambda, 0 mm midline, and 1 mm ventral to the skull surface, with the mouth bar set at −3.3.

Brain Samples

Transgenic MJD Q69 mice (n=6) and age-matched wild-type littermates (n=6) were sacrificed at three months of age. The animals, given an overdose of sodium pentobarbital, were perfused transcardially with ice-cold PBS 0.1M before brain extraction. For western-blot processing, the cerebellum and the "rest of the brain" of the left cerebral hemisphere was dissected and then homogenized in a lysis buffer (TBS, NaCl 150 mM and Triton 1%) containing phosphatase (Pierce) and protease (Roche) inhibitors. After centrifugation (20 min, 13 000 rpm, 4° C.), the supernatant was collected and the protein concentration was quantified (BCA Protein Assay, Thermo Fisher Scientific, Waltham, USA). Lysate aliquots (3 mg of protein/ml) were stored at −80° C. until use. The cerebellum and the "rest of the brain" of the left cerebral hemisphere was dissected and conserved at −80° C. until GC-MS analysis. In addition, C57Bl/6 mice (n=8) injected with viral vectors were perfused transcardially with ice-cold PBS 0.1M, followed by 4% paraformaldehyde (PFA) in 0.1M PBS, before brain extraction. Brains were post-fixed in 4% PFA in 0.1M PBS for 3 days and cryoprotected by incubation in a 20% sucrose/0.1 M PBS solution. Coronal brain sections (25 µm) were cut on a freezing microtome (Leica, Wetzlar, Germany), collected serially, and stored at 4° C., free-floating in 0.02% sodium azide PBS until immunohistochemical processing. The brains of transgenic MJD Q69 mice injected with AAVrh10-CYP46A1 or AAVrh10-GFP and age-matched wild-type mice were removed, post-fixed in 4% PFA for 24 h and cryoprotected by incubation in 25% sucrose/phosphate buffer for 48 h. Subsequently, brains were frozen and sagittal sectioned (40 µm sections) using a cryostat (LEICA CM3050 S).

Behavioral Tests in Transgenic MJD Mice

To evaluate the impact of AAVrh10-CYP46A1 overexpression on the motor phenotype, transgenic MJD mice (C57BL/6 background) were injected with AAVrh10-CYP46A1 (n=10) or either AAVrh10-GFP (control) (n=9); in addition, four littermate wild-type animals were used. Mice were trained on a battery of motor tests, starting at 5-6 weeks of age, and performed every 4 weeks, starting from week 2 after injection until 10 weeks post-injection. Experiments were assessed by an experienced operator in a blind-fashion manner. All tests were performed in the same dark room after 30 min of acclimatization.

Rotarod

Motor coordination and balance were evaluated with a Rotarod apparatus (Letica Scientific Instruments). Mice were placed on the Rotarod apparatus (Letica Scientific Instruments), at a constant speed (5 rpm) for a maximum of 5 min and/or at accelerated speed (4-40 rpm, in 5 min) and the latency to fall was recorded. All tests were performed in the same dark room after 30 min of acclimatization. Mice performed four trials for each time point with a 15-20 min rest between trials. For analysis, the mean latency to fall off the Rotarod of three trials was used. Mice were trained and performed this test every 2/4 weeks until 10 weeks after the beginning of the treatment. An experienced operator performed the tests in a blind-fashion manner.

Footprint Pattern Analysis

The footprint pattern (walking tracks) test was used to compare the gait of mice injected with AAVrh10-CYP46A1 with mice injected with AAVrh10-GFP. Thus, hind and fore feet were coated with red and blue non-toxic paints, respectively. Animals were placed in the floor of a runway (with 15-cm high walls) and walked along a 100-cm long and 10-cm wide sheet of white paper. The footprint patterns were analyzed for the distance between sequential footprints of hind limbs, measured orthogonal to the walking direction. The base between the center of the hind footprint and the center of the preceding hind footprint (hind base) was recorded over a sequence of five consecutive steps, excluding footprints made at the beginning and end of the run.

Cholesterol and Oxysterol Measurements

Cholesterol and oxysterol analysis followed the 'gold standard' method (Dzeletovic et al., 1995) to minimize the formation of autoxidation artefacts. Briefly, mouse striatal tissue samples were weighed and homogenized with a TissueLyser II apparatus (Qiagen) in a 500 µl solution containing butylated hydroxytoluene (BHT, 50 µg/ml) and EDTA (0.5 M). At this point, a mix of internal standards was added [epicoprostanol, $^2H_7$-7-lathosterol, $^2H_6$-desmosterol, $^2H_6$-lanosterol and $^2H_7$-24(R/S)-hydroxycholesterol] (Avanti Polar Lipids). Alkaline hydrolysis was performed under Ar using 0.35 M ethanolic KOH for 2 h at room temperature. After neutralization of the solution with phosphoric acid, sterols were extracted in chloroform. The lower phase was collected, dried under a stream of nitrogen and the residue was dissolved in toluene. Oxysterols were then separated from the cholesterol and its precursors on a 100 mg Isolute silica cartridge (Biotage); cholesterol was eluted in 0.5% propan-2-ol in hexane followed by oxysterols in 30% propan-2-ol in hexane. The sterol and oxysterol fractions were independently silylated with Regisil®+10% TMCS [bis(trimethylsilyl) trifluoro-acetamide+10% trimethylchlorosilane] (Regis technologies) as described previously (Chevy et al., 2005). The trimethylsilylether derivatives of sterols and oxysterols were separated by gas chromatography (Hewlett-Packard 6890 series) in a medium polarity capillary column RTX-65 (65% diphenyl 35% dimethyl polysiloxane, length 30 m, diameter 0.32 mm, film thickness 0.25 µm; Restesk). The mass spectrometer (Agilent 5975 inert XL) in series with the gas chromatography was set up for detection of positive ions. Ions were produced in the electron impact mode at 70 eV. They were identified by the fragmentogram in the scanning mode and quantified by selective monitoring of the specific ions after normalization and calibration with the appropriate internal and external standards [epicoprostanol m/z 370, $^2H_7$-7-lathosterol m/z 465, $^2H_6$-desmosterol m/z 358, $^2H_6$-lanosterol m/z 504, $^2H_7$-24(R/S)-hydroxycholesterol m/z 553, cholesterol m/z 329, 7-lathosterol m/z, 7-dehydrocholesterol m/z 325, 8-dehydrocholesterol m/z 325, desmosterol m/z 343, lanosterol m/z 393 and 24(R/S)-hydroxycholesterol m/z 413].

Western Blot

Total protein concentrations were determined using the BCA kit (Pierce). Equal amounts of total protein extract (30 µg) were electrophoretically separated using SDS-PAGE in 4-12% Bis-Tris gels (NuPAGE® Novex Bis-tris midi gel 15 or 26 wells, Life Technologies, Carlsbad, USA) and transferred to nitrocellulose membranes. Blocked membranes (5% non-fat dry milk in TBS-0.1% Tween-20) were incubated with primary antibodies overnight at 4° C., and washed three times with TBS-0.1% Tween-20 (T-BST) for 10 min. Membranes were then labeled with secondary IgG-HRP antibodies raised against each corresponding primary antibody. After three washes with T-BST, the membranes were incubated with ECL chemiluminescent reagent (Clarity Western ECL substrate; GE Healthcare, Little Chalfont, UK) according to the instructions of the supplier. Peroxydase activity was detected with camera system Fusion TX7 (Fisher Scientific). Normalization was done by densitometry analysis with the Quantity One 1D image analysis software (version 4.4; Biorad, Hercules, CA, USA). The optical densities were normalized with respect to a "standard protein" (GAPDH). A partition ratio was calculated and normalized with respect to the sample with the highest value defined as 1.

Primary Antibodies

Antibodies used in western-blot (WB) and immunohistochemical (IHC) analyses are listed in table 1, below.

TABLE 1

Antibodies used in western-blot (WB) and immunohistochemical (IHC) analyses

| Primary antibodies | Source | WB | IHC |
|---|---|---|---|
| mouse anti-ATXN3 (clone 1H9) | Millipore | — | 1:2000 |
| mouse anti hemagglutinin tag | Covance | 1:4000 | 1:5000 |
| rabbit anti-ubiquitin | Dako | — | 1:3000 |
| rabbit anti-CYP46A1 | Abcam | 1:2000 | 1:3000 |
| rabbit anti-DARPP32 | Millipore | — | 1:2000 |
| rabbit anti-GFP | Abcam | — | 1:5000 |
| mouse anti-GAPDH | Abcam | 1:4000 | — |
| rabbit anti-LC3B | Cell Signalling | 1:1000 | — |
| mouse anti-tubulin | Sigma | 1:5000 | — |

Immunostaining

The immunohistochemical procedure was initiated, by quenching endogenous peroxidase by incubating free-floating sections in phenylhydrazine for 25 min at 37° C. After three washes, slices were blocked in PBS/0.1% Triton X-100 containing 10% Normal Goat Serum (NGS, Gibco) for 1 h at RT. The sections were then incubated with the respective primary antibodies, overnight at 4° C. After three washings, the sections were incubated with the corresponding biotinylated secondary antibody (1:250; Vector Laboratories Inc., CA, USA) diluted in PBS/0.1% Triton X-100 and 10% NGS for 2 h at RT. After three washes, bound antibodies were visualized by the ABC amplification system (Vectastain ABC kit, Vector Laboratories, West Grove, USA) and 3,3'-diaminobenzidine tetrahydrochloride (peroxidase substrate kit, DAB, Vector Laboratories, CA, USA) as the substrate. The sections were mounted, dehydrated by passing twice through ethanol and toluol solutions, and coverslipped with Eukitt® (O. Kindler GmbH & CO, Freiburg, Germany).

Image Acquisition

Images of immunostained sections were acquired with a Z6 APO macroscope (Leica) and LAS V3.8 (Leica) software, at room temperature, with a brightfield Leica DM 5000B microscope equipped with a Leica DFC310FX digital camera. Photographs for comparison were taken under identical conditions of image acquisition, and all adjustments of brightness and contrast were applied uniformly to all images.

Immunohistochemical Quantitative Analysis of ATXN3 Aggregates and DARPP-32 Depletion in the LV-Based Model of MJD Brain slices were analyzed and imaged at RT with an Axiovert 200M microscope (CCD color digital Axiocam HRc camera; Carl Zeiss), at 5× (air objective, Fluar, 0.25 NA) and 20× magnifications (air objective, LD-PlanNeofluar, 0.4 NA). Composite images of complete aggregate-containing or DARPP-32-depleted regions were automatically acquired using the MozaiX function of the AxioVision software. Quantification of ATXN3-positive aggregates and determination of the area of the DARPP-32 depletion was made in 7-8 slices for each mouse, spread over the anterior-posterior extent of the striatum and separated by 200 µm. Counting of ATXN3-positive aggregates was performed on 20×-magnified images of each hemisphere using ImageJ (National Institutes of Health). After manually thresholding images so that the recognizable ATXN3-positive accumulations were included in the examination, particles >3 µm² were automatically analyzed and counted (scale: 2 pixels/µm), and the estimative calculation of the total number of aggregates in the entire striatum was performed as previously described (Alves et al., 2008a; Alves et al., 2010). The extent of MUT ATXN3 lesions in the striatum was analyzed by digitizing 6-8 DARPP-32-stained sections per animal (200 µm between 25 µm thickness sections), selected to obtain a complete rostro-caudal sampling of the striatum with a slide scanner and by quantifying the area of the lesion with a semiautomated image-analysis program (ImageJ software, NIH, MD, USA), to manually define the regions with decreased antibody reactivity and quantify their area (scale: 0.5 pixels/µm). Sections throughout the entire striatum were analyzed. The area of the striatum showing a loss of DARPP-32 staining was measured for each animal with an operator-independent macro. The volume was then estimated using the following formula: volume=d(a1+a2+a3+ . . . ), where d is the distance between serial sections (200 µm), and a1, a2, a3 etc. are DARPP-32-depleted areas for individual serial sections (Alves et al., 2008b). The average gray value of all pixels measured in the lesioned area was recorded for each depleted area. Results are presented as the calculated value for volume of the DARPP-32 depleted region for each animal. In all cases, imaging, measurements, and quantifications were performed blindly to the treatment.

Immunohistochemistry Quantitative Analysis in the MJD Transgenic Mice

Quantification of Cerebellar Volume:

The cerebellar volume was blindly assessed by scanning the area per lobe in 8 sections stained with cresyl violet, covering the full extent of the cerebellum. The cerebellar volume was obtained by multiplying the total area by the distance between serial sections (320 µm).

Quantification of Granular and Molecular Layers Size:

Quantification was made over 4 cresyl violet staining sections spread over the anterior-posterior extent of the cerebellum in a blind fashion using a 20× objective. For each section the size of the layers was assessed blindly per lobe in 3 to 5 different measurements (depending on the lobe size).

Quantification of Purkinje Cells:

Fluorescence images of 8 sagittal sections covering entire cerebellum, stained with anti-Calbindin and DAPI were acquired with a Zeiss Axio Imager Z2 microscope using a 20× objective. For each section and the number of Purkinje cells were manually counted for each cerebellar lobe in a blind fashion way. Data is represented as mean value of the number of Purkinje cells in the entire cerebellum or per lobe.

Quantification of Ubiquitin Aggregates:

The number of ubiquitin aggregates was assessed in lobes 9 and 10 automatically using Cell Profiler software, from images 8 sagittal sections covering entire cerebellum, stained with anti-ubiquitin and DAPI were acquired with a Zeiss Axio Imager Z2 microscope using a 20× objective. The analysis modules applied were the same for all the animals and images. Data is represented as the average number of ubiquitin aggregates per section.

Cresyl Violet Staining

Cerebellar sections were stained with cresyl violet for 2 minutes, differentiated in acetate buffer pH 3.8 to 4 (2.72% sodium acetate and 1.2% acetic acid; 1:4 v/v), dehydrated by passing twice through ethanol and toluol solutions, and mounted with Eukitt® (O. Kindler GmbH & CO. Freiburg, Germany).

Neuroblastoma Cell Culture and Transfection

Mouse neuroblastoma cell line (N2a cells) obtained from the American Type Culture Collection cell biology bank (CCL-131) were maintained in Dulbecco's modified Eagle's medium (DMEM) supplemented with 10% foetal bovine serum (FBS), 100 U/ml penicillin and 100 mg/ml streptomycin (Gibco) at 37° C. in 5% $CO_2$/air atmosphere. The human full-length mutant Atx3 with 84 glutamines (pEGFP-Atx3Q84; (Chai et al., 2002) was transfected in the Neuro2A cells using PEI (Polyethylenimine) and a total concentration of 0.5 mg of each DNA. Cells were lysed for western blot processing 48 hours post-transfection.

Autophagic Flux Measurement

The autophagic flux was measured through the LC3B turnover assay, which is used to quantify the amount of LC3B-II that is delivered to the lysosomes (Aveleira et al., 2015). For that purpose, the levels of LC3B-II were measured in the presence and absence of chloroquine (ChQ, SIGMA, 100 µm), an inhibitor of autolysosomal degradation. The autophagic flux was calculated by subtracting the densitometric value of LC3B-II in samples without chloroquine (LC3B-II−ChQ) from the corresponding sample treated with chloroquine (LC3B-II+ChQ) for each condition.

Statistical Analysis

Statistical analysis was performed using the Mann-Whitney test and paired or unpaired Student's t-test or ANOVA for multiple comparisons. Results are expressed as mean±SEM. Significant thresholds were set at $P<0.05$, $P<0.01$ and $P<0.001$, as defined in the text. All analyses were performed using GraphPad Prism (GraphPad Software, La Jolla, USA).

Results

Decreased Levels of CYP46A1 Protein Levels in the Cerebellum of MJD Transgenic Mice The levels of CYP46A1 was evaluated in frozen biopsies from six MJD transgenic mice expressing the N-terminal truncated human ATXN3, with 69 CAG repeats and six age-matched control littermates by western-blot. In particular, CYP46A1 protein levels was analyzed in the cerebellum, since mutant human ataxin-3 was specifically expressed in cerebellar Purkinje cells (Oue et al., 2009). As control region, the "rest of the brain" (all brain tissue excepting the cerebellum) was used, in which no expression of mutant human ataxin-3 was detected (FIG. 1). Western-blot analysis demonstrated a 24.3% reduction in CYP46A1 protein levels (Mann-Whitney test; p=0.026) in cerebellar biopsies from MJD mice relatively to control littermates (FIGS. 2A and B). In the contrary, no statistical significant differences were found in extracts from the "rest of the brain" among MJD mice and control littermates (Mann-Whitney test; p=0.13) (FIGS. 2C and D).

Overall, these data support the relevance of CYP46A1, a key enzyme in cholesterol metabolism pathway, as a therapeutic target in human spinocerebellar ataxias, in particular, MJD.

Deregulation of the Cholesterol Metabolism Pathway in the Brain of MJD Transgenic Mice To determine the impact of CYP46A1 deficiency in MJD, the cholesterol metabolism was analyzed by performing quantitative measurements of both sterols and oxysterols by gas-chromatography mass spectrometry (GC/MS) in cerebellar extracts from MJD Q69 mice and age-matched littermates. Therefore, lanosterol, the first sterol of the cholesterol metabolic pathway, along with cholesterol intermediates from the Kandutsch-Russell (lathosterol) and Bloch (desmosterol) pathways were measured. The cholesterol and 24S—OHC content were first compared and a statistically significant reduction (21.3%) was observed in the levels of 24S—OHC in MJD Q69 mice (20.62±1.14 µg/g; n=6) relatively to wild-type littermates (26.19±0.78 µg/g; n=6, Student's T test, P=0.002) (FIG. 3A). No statistically significant differences were observed for the cerebellar cholesterol content among MJD mice and wild-type mice (FIG. 3A). No statistically significant differences were found for the oxysterols 25S—OHC and 27S—OHC and for the remaining sterols (lanosterol, 7-lathosterol, desmosterol, 7-DHC and 8-DHC) (FIG. 3A).

As mutant human ataxin-3 is only expressed in cerebellar Purkinje cells, the "rest of the brain" was used to measure the levels of the above referred oxysterols and sterols. Surprisingly, a statistically significant increase was detected in the levels of 24S—OHC in the "rest of the brain" from MJD Q69 mice (6.32±0.40 µg/g; n=6), relatively to control littermates (4.68±0.37 µg/g; n=6; Student's T test, P=0.013) (FIG. 3B). A statistically significant augmentation was also found in the levels of cholesterol in MJD Q69 mice (10.74±0.41 mg/g; n=6) compared to wild-type mice (8.68±0.53 mg/g; n=6; Student's T test, P=0.011) (FIG. 3B). The levels of the cholesterol precursor desmosterol were increased in MJD Q69 mice (243.0±14.93 µg/g; n=6) relatively to wild-type mice (172.5±14.6 µg/g; n=6; Student's T test, P=0.007), as well as, the levels of 7-lathosterol (4.68±0.37 µg/g in normal mice; n=6 vs 6.32±0.40 µg/g in MJD Q69 mice; n=6; Student's T test, P=0.054) (FIG. 3B). In the same line, the levels of lanosterol were slightly increased in MJD Q69 mice (4.30±0.30 µg/g; n=6) as compared to wild-type mice (3.46±0.29 µg/g; n=6, Student's T test, P=0.07) (FIG. 3B). No statistical significant differences were found for the 7-dehydrocholesterol (7-DHC) and for the 8-dehydrocholesterol (8-DHC). In addition, the levels of the oxysterol 27-OHC were decreased in MJD Q69 mice (0.21±0.035 µg/g; n=6) relatively to wild-type mice (0.60±0.07 µg/g; n=6; Student's T test P=0.0006). No differences were observed for 25-OHC levels among MJD Q69 and wild-type mice (FIG. 3B).

Altogether, these results suggest alterations in the cholesterol metabolism pathway in MJD affected regions like the cerebellum (in which mutant ATXN3 is specifically expressed) and also in regions in which no mutant ATXN3 is detected (rest of the brain).

CYP46A1 Overexpression Alleviates Neuropathology in an MJD LV-Based Mouse Model

The invention then investigated whether the upregulation of the cholesterol metabolism pathway, through increase in the levels of CYP46A1, could improve mutant ataxin-3 clearance, therefore delaying the establishment of MJD-associated neuropathology. Next, the therapeutic effect of CYP46A1 overexpression in the LV-based mouse model of MJD was evaluated (Alves et al., 2008b; Nobrega et al., 2013). For this purpose, LV encoding mutant human ataxin-3 and an AAV encoding CYP46A1 were co-expressed in the striatum of an MJD mouse model and sacrificed the mice two months post-injection. HA-directed immunohistochemistry revealed the presence of the HA tag in AAVrh.10-CYP46A1-injected LV-MJD mice but not in the control group injected with AAVrh.10-GFP (FIG. 4A). Conversely, in mice injected with AAVrh.10-GFP, a robust and widespread GFP immunoreactivity was detected in the mouse brain, whereas no HA-positive signals were detected (FIG. 4A).

In the MJD mouse model, immunohistochemistry (with the 1H9 antibody) and quantitative analysis for mutant ataxin-3-positive inclusions (FIG. 4A) revealed a statistically significant CYP46A1-mediated decrease (~59%) in the number of ataxin-3-positive inclusions (2751±267.8; n=8) compared to the control group (GFP-co-injected mice; 6684±717.2 inclusions; n=8; Student's T test, P=0.0002) (FIG. 4B). The surface of inclusions was also analyzed and demonstrated a statistically significant decrease in the size of inclusions (~47%) in AAVrh.10-CYP46A1 treated LV-MJD mice (59.29±4.67 arbitrary units (a.u.); n=8) compared to LV-MJD mice injected with the control AAVrh.10-GFP (111.4±3.96 a.u.; n=8; Student's T test, P<0.0001) (FIG. 4B). These results were completed with anti-ubiquitin immunostaining that demonstrated a reduction in the number of ubiquitinated inclusions in LV-MJD mice injected with AAVrh.10-CYP46A1 relatively to LV-MJD mice in which the control AAVrh.10-GFP was injected (FIG. 4A). In view of these results, whether mutant human ataxin-3 clearance would confer neuroprotection in the LV-MJD mouse model was next inspected. It has been reported that LV-based mutant ataxin-3 overexpression in the mouse striatum promotes depletion of the neuronal marker DARPP-32, that can be precisely quantified (Alves et al., 2008b). Therefore immunohistochemistry for DARPP-32 was performed (FIG. 4D). CYP46A1 overexpression led to a statistically significant reduction (~48%) of neuronal dysfunction, as assessed by decreased DARPP-32 depleted region at 2 months (0.48±0.77 mm$^3$; n=8) relatively to LV-MJD mice injected with control AAVrh.10-GFP (0.91±0.14 mm$^3$; n=8) Student's T test; P=0.015).

Overall, these data support that CYP46A1 overexpression has therapeutic properties, promoting the clearance of misfolded mutant human ataxin-3, therefore conferring preservation of neuronal markers and neuroprotection in an LV-MJD mouse model.

AAV-Mediated CYP46A1 Gene Therapy Improves Neuropathology and Motor Coordination in MJD Transgenic Mice Next investigation if CYP46A1 upregulation would alleviate motor and cerebellar deficits after the onset of the disease was performed, by using a transgenic MJD mouse model (Torashima et al., 2008). This model is characterized by a strong motor and neuropathological phenotype and particularly suitable for testing molecular therapies (Nobrega et al., 2014; Mendonca et al., 2015; Nobrega et al., 2015). To assess the potential of CYP46A1 overexpression to improve the motor phenotype of MJD-transgenic mice with severe motor impairments, AAVrh10 encoding for CYP46A1, or GFP (control), were injected into the cerebellum of adult MJD-transgenic mice and the motor performance was evaluated every 2/4 weeks until 10 weeks after the virus injection. Using rotarod test at constant speed (FIG. 5A) and accelerated rotarod test (FIG. 5B) it was observed that at the time of the injection the MJD-transgenic mice already displayed marked motor impairments, as compared to wild-type mice (WT). Moreover, throughout the study the mice expressing CYP46A1 have a better motor performance as compared to GFP mice, although, only at 10 weeks after AAV injection the different latency to fall observed between mice expressing CYP46A1 and GFP became significant (FIG. 5A, CYP 53.07 s versus GFP 17.48 s) for both rotarod tests. This improvement in the motor function was further analyzed with foot printing pattern test, namely the hind base test. It was observed that mice treated with AAVrh10-CYP46A1 have a tendency for a better hind base performance at 10 weeks after the virus injection (FIG. 5C, AAVrh10-CYP46A1: 3.17±0.07 cm versus AAVrh10-GFP: 3.40±0.11 cm); however no significant difference was observed between both groups with this test.

To investigate whether the improvements in motor function were also related with neuronal improvements, the aggregates number and the cerebellar neuropathology of the injected mice were next evaluated. Like in (Nobrega et al., 2013b; Nobrega et al., 2014), the transduction of viral vectors was preferentially detected on lobes IX and X of cerebellar cortex. In accordance with behavioural data, the average number ubiquitin aggregates were significantly reduced in transduced lobes in AAVrh10-CYP46A1-injected mice compared with AAVrh10-GFP-injected controls (FIG. 6). This transgenic mouse model is characterized by a loss of Purkinje cells and a strong disorganization of cerebellar cortex (Oue et al., 2009). Importantly, the average number of Purkinje cells was significantly higher in animals injected with AAVrh10-CYP46A1 compared to the controls (FIG. 6). Moreover, the cerebellar volume was higher in lobe IX and X in AAVrh10-CYP46A1-injected mice, as well as the thickness of granular layer (FIG. 6). Altogether these data show that CYP46A1 upregulation mediates a robust alleviation of motor phenotype and neuropathological abnormalities in a severe-progressive MJD transgenic mouse model.

CYP46A1 Overexpression Induces Autophagy and Clears Mutant ATXN3 in Neuro2A Cells The molecular mechanism of CYP46A1 action and its impact in Neuro2A cells expressing mutant ATXN3 (EGFP-Q84) were next investigated. The analysis of mutant ATXN3 species levels by western blot revealed that CYP46A1 overexpression significantly reduce those levels compared to control conditions (FIG. 7A), both in aggregates (1±0.0 vs 0.449±0.11; n=4; FIG. 7B), as well as in the soluble protein (1±0.0 vs 0.09±0.06; n=4; FIG. 7C). Based on these results, investigations were next performed to determine if CYP46A1 was reducing mutant ATXN3 through autophagy, as a main cellular pathway for clearing aggregated species (FIG. 8A). In fact, it was found that CYP46A1 overexpression significantly increased LC3B-II levels (2.12±0.35; n=4) comparing to the control condition (1±0.0; n=4). This increase in the LC3B-II levels was even higher upon CYP46A1 overexpression compared to the starvation condition (autophagy positive control; 1.58±0.02; n=4) (FIG. 8B). Moreover, in the presence of the autophagy inhibitor (chloroquine-ChQ) the results observed follow the same trend, i.e., an increase in LC3B-II levels upon CYP46A1 overexpression (6.74±1.31; n=4) compared to control condition (2.83±0.44; n=4) (FIG. 8B). Moreover, CYP46A1 overexpression significantly increased the autophagic flux, highlighted by an increase in the LC3B-II net flux (2.80±0.16; n=4) comparing to the control condition (1±0.0; n=4) (FIG. 8C).

Altogether these results show that CYP46A1 is a strong modulator of mutant ATXN3, reducing its levels through a robust activation of the autophagy pathway.

Thus, it was demonstrated that CYP46A1 levels are decreased in cerebellar extracts from MJD/PolyQ mice. It was also showed that overexpression of AAVrh10-CYP46A1 in a lentiviral-based animal mouse model of MJD conferred neuroprotection by reducing mutant human ataxin-3 accumulation, associated to the preservation of neuronal markers. This was confirmed in adult MJD transgenic mice, in which cerebellar AAVrh10-CYP46A1 overexpression induced a noteworthy alleviation of motor behavior impairments correlated with mitigation of MJD-associated neuropathology, in particular, decrease of misfolded protein and reduction of Purkinje cell loss and of cellular layer shrinkage in the cerebellum. Thus, AAV-CYP46A1 reduces the accumulation of misfolded ataxin-3 alleviating MJD-associated neuropathology, therefore improving motor behavior defects.

Remarkably, it was demonstrated in neuroblastoma cells that CYP46A1 activates autophagy decreasing mutant ATXN3 deposition.

Therefore, these results support CYP46A1 as a relevant therapeutic target for SCAs.

REFERENCES

Alves, S., et al., 2008a. Allele-specific RNA silencing of mutant ataxin-3 mediates neuroprotection in a rat model of Machado-Joseph disease. PLoS One. 3, e3341.

Alves, S., et al., 2008b. Striatal and nigral pathology in a lentiviral rat model of Machado-Joseph disease. Hum Mol Genet. 17, 2071-83.

Alves, S., et al., 2010. Silencing ataxin-3 mitigates degeneration in a rat model of Machado-Joseph disease: no role for wild-type ataxin-3? Hum Mol Genet. 19, 2380-94.

Bjorkhem, I., et al., 1998. Cholesterol homeostasis in human brain: turnover of 24S-hydroxycholesterol and evidence for a cerebral origin of most of this oxysterol in the circulation. J Lipid Res. 39, 1594-600.

Burk, K., et al., 1999. Autosomal dominant cerebellar ataxia type I: oculomotor abnormalities in families with SCA1, SCA2, and SCA3. J Neurol. 246, 789-97.

Chevy, F., Humbert, L., Wolf, C., 2005. Sterol profiling of amniotic fluid: a routine method for the detection of distal cholesterol synthesis deficit. Prenat Diagn. 25, 1000-6.

Durr, A., et al., 1996. Spinocerebellar ataxia 3 and Machado-Joseph disease: Clinical, molecular, and neuropathological features. Annals of Neurology. 39, 490-499.

Dzeletovic, S., et al., 1995. Time course of oxysterol formation during in vitro oxidation of low density lipoprotein. Chem Phys Lipids. 78, 119-28.

Hudry, E., et al., 2010. Adeno-associated virus gene therapy with cholesterol 24-hydroxylase reduces the amyloid pathology before or after the onset of amyloid plaques in mouse models of Alzheimer's disease. Mol Ther. 18, 44-53.

Kawaguchi, Y., et al., 1994. CAG expansions in a novel gene for Machado-Joseph disease at chromosome 14q32.1. Nat Genet. 8, 221-8.

Kotin, et al. 1994. Parvoviridae and their Replication. Fundamental Virology.

Klockgether, T., et al., 1998. Autosomal dominant cerebellar ataxia type I. MRI-based volumetry of posterior fossa structures and basal ganglia in spinocerebellar ataxia types 1, 2 and 3. Brain. 121 (Pt 9), 1687-93.

Lukas C., et al., 2008. Spinal cord atrophy in spinocerebellar ataxia type 3 and 6: impact on clinical disability. J Neurol. 2008 August; 255(8):1244-9. doi: 10.1007/s00415-008-0907-6. Epub 2008 Jun. 5.

McCarty, D M., et al., 2001. Self-complementary recombinant adeno-associated virus (scAAV) vectors promote efficient transduction independently of DNA synthesis. gene Ther. 2001 August; 8(16):1248-54.

Nobrega, C., et al., 2013. Overexpression of mutant ataxin-3 in mouse cerebellum induces ataxia and cerebellar neuropathology. Cerebellum. 12, 441-55.

Orr, H. T., Zoghbi, H. Y., 2007. Trinucleotide repeat disorders. Annu Rev Neurosci. 30, 575-621.

Oue, M., et al., 2009. Characterization of mutant mice that express polyglutamine in cerebellar Purkinje cells. Brain Res. 1255, 9-17.

Rub, U., et al., 2006. Degeneration of ingestion-related brainstem nuclei in spinocerebellar ataxia type 2, 3, 6 and 7. Neuropathol Appl Neurobiol. 32, 635-49.

Rub, U., Brunt, E. R., Deller, T., 2008. New insights into the pathoanatomy of spinocerebellar ataxia type 3 (Machado-Joseph disease). Curr Opin Neurol. 21, 111-6.

Schols, L., et al., 1997. Autosomal dominant cerebellar ataxia: phenotypic differences in genetically defined subtypes? Ann Neurol. 42, 924-32.

Schols, L., et al., 2004. Autosomal dominant cerebellar ataxias: clinical features, genetics, and pathogenesis. Lancet Neurol. 3, 291-304.

Torashima, T., et al., 2008. Lentivector-mediated rescue from cerebellar ataxia in a mouse model of spinocerebellar ataxia. EMBO Rep. 9, 393-9.

Benjamin E. Deverman et al., 2016. Cre-dependent selection yields AAV variants for widespread gene transfer to the adult brain. Nat Biotechnol. 34(2):204-209.

The invention claimed is:

1. A method of treatment of a Polyglutamine repeat spinocerebellar ataxia, comprising administering a vector which comprises cholesterol 24-hydroxylase encoding nucleic acid to a patient in need thereof.

2. The method of treatment of a Polyglutamine repeat spinocerebellar ataxia according to claim 1, wherein the Polyglutamine repeat spinocerebellar ataxia is selected from the group of Spinocerebellar ataxia type 1 (SCA1), Spinocerebellar ataxia type 2 (SCA2), Spinocerebellar ataxia type 3 (SCA3), Spinocerebellar ataxia type 6 (SCA6), Spinocerebellar ataxia type 7 (SCA7) and Spinocerebellar ataxia type 17 (SCA17).

3. The method of treatment of a Polyglutamine repeat spinocerebellar ataxia according to claim 1, wherein the Polyglutamine repeat spinocerebellar ataxia is Spinocerebellar ataxia type 3 (SCA3).

4. The method of treatment of a Polyglutamine repeat spinocerebellar ataxia according to claim 1, wherein the vector comprises a nucleic acid sequence that encodes the amino acid sequence SEQ ID NO: 2.

5. The method of treatment of a Polyglutamine repeat spinocerebellar ataxia according to claim 1, wherein the vector comprises the nucleic acid sequence SEQ ID NO: 1.

6. The method of treatment of a Polyglutamine repeat spinocerebellar ataxia according to claim 1, wherein the vector is selected from the group of adenovirus, lentivirus, retrovirus, herpesvirus and Adeno-Associated Virus (AAV) vectors.

7. The method of treatment of a Polyglutamine repeat spinocerebellar ataxia according to claim 1, wherein the vector is an AAV vector.

8. The method of treatment of a Polyglutamine repeat spinocerebellar ataxia according to claim 7, wherein the vector is an AAV9 or AAV10 vector.

9. The method of treatment of a Polyglutamine repeat spinocerebellar ataxia according to claim 7, wherein the vector is an AAVrh.10.

10. The method of treatment of a Polyglutamine repeat spinocerebellar ataxia according to claim 1, wherein the vector is administered directly into the brain of the patient.

11. The method of treatment of a Polyglutamine repeat spinocerebellar ataxia according to claim 9, wherein the vector is administered in at least a region of the brain selected from the group of cerebellum, brainstem, substantia nigra, striatum, frontotemporal lobes and visual cortex.

12. The method of treatment of a Polyglutamine repeat spinocerebellar ataxia according to claim 1, wherein the vector is administered into the spinal cord of the patient.

13. The method of treatment of a Polyglutamine repeat spinocerebellar ataxia according to claim 1, wherein the vector is administered by intravascular, intravenous, intranasal, intraventricular or intrathecal injection.

14. The method of treatment of a Polyglutamine repeat spinocerebellar ataxia according to claim 1, comprising the administration of a pharmaceutical composition which comprises a therapeutically effective amount of the vector to the patient.

* * * * *